US010072065B2

(12) United States Patent
Sarkar et al.

(10) Patent No.: US 10,072,065 B2
(45) Date of Patent: Sep. 11, 2018

(54) PEPTIDE-MEDIATED DELIVERY OF IMMUNOGLOBULINS ACROSS THE BLOOD-BRAIN BARRIER

(71) Applicant: Mayo Foundation for Medical Education and Research, Rochester, MN (US)

(72) Inventors: Gobinda Sarkar, Rochester, MN (US); Robert B. Jenkins, Rochester, MN (US); Geoffry L. Curran, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 9 days.

(21) Appl. No.: 15/246,232

(22) Filed: Aug. 24, 2016

(65) Prior Publication Data

US 2017/0058017 A1 Mar. 2, 2017

Related U.S. Application Data

(60) Provisional application No. 62/209,052, filed on Aug. 24, 2015.

(51) Int. Cl.

| | |
|---|---|
| ***C07K 14/775*** | (2006.01) |
| ***C07K 16/28*** | (2006.01) |
| ***A61K 47/64*** | (2017.01) |
| ***A61K 39/00*** | (2006.01) |

(52) U.S. Cl.

CPC ............ *C07K 14/775* (2013.01); *A61K 47/64* (2017.08); *C07K 16/2863* (2013.01); *A61K 2039/505* (2013.01); *C07K 2317/24* (2013.01)

(58) Field of Classification Search

None

See application file for complete search history.

(56) References Cited

U.S. PATENT DOCUMENTS

| | | | |
|---|---|---|---|
| 4,647,447 | A | 3/1987 | Gries et al. |
| 5,168,045 | A | 12/1992 | Dyer et al. |
| 5,591,721 | A | 1/1997 | Agrawal et al. |
| 5,652,356 | A | 7/1997 | Agrawal |
| 5,807,746 | A | 9/1998 | Lin et al. |
| 6,245,751 | B1 | 6/2001 | Crutcher et al. |
| 6,509,154 | B1 | 1/2003 | de Paillette |
| 8,877,726 | B2 | 11/2014 | Kreutzer et al. |
| 9,597,408 | B2 | 3/2017 | Curran et al. |
| 2002/0009491 | A1 | 1/2002 | Rothbard et al. |
| 2002/0173456 | A1 | 11/2002 | Smith et al. |
| 2003/0118610 | A1 | 6/2003 | Stern et al. |
| 2004/0072774 | A1 | 4/2004 | Manfredi et al. |
| 2004/0229219 | A1 | 11/2004 | Gallaher et al. |
| 2004/0241164 | A1 | 12/2004 | Bales et al. |
| 2005/0053591 | A1 | 3/2005 | Pun |
| 2005/0118204 | A1 | 6/2005 | Sakamoto et al. |
| 2005/0169904 | A1 | 8/2005 | Payne |
| 2006/0153834 | A1 | 7/2006 | Carbonell et al. |
| 2006/0198833 | A1 | 9/2006 | Verma et al. |
| 2006/0229246 | A1 | 10/2006 | Hawley-Nelson et al. |
| 2007/0086981 | A1 | 4/2007 | Meijer et al. |
| 2008/0213185 | A1 | 9/2008 | Hong et al. |
| 2010/0119528 | A1 | 5/2010 | Sarkar et al. |
| 2011/0312877 | A1 | 12/2011 | Berninger et al. |
| 2012/0107243 | A1 | 5/2012 | Curran et al. |
| 2014/0314663 | A1 | 10/2014 | Sarkar et al. |
| 2014/0328866 | A1 | 11/2014 | Curran |
| 2016/0106858 | A1* | 4/2016 | Hall ...................... C07K 16/18 424/450 |
| 2017/0007669 | A1 | 1/2017 | Sarkar et al. |
| 2017/0145076 | A1 | 5/2017 | Curran et al. |

FOREIGN PATENT DOCUMENTS

| | | |
|---|---|---|
| WO | WO 1999007409 | 2/1999 |
| WO | WO 1999032619 | 7/1999 |
| WO | WO 1999064449 | 12/1999 |
| WO | WO 2000001846 | 1/2000 |
| WO | WO 2000044895 | 8/2000 |
| WO | WO 2000044914 | 8/2000 |
| WO | WO 2001029058 | 4/2001 |
| WO | WO 2001036646 | 5/2001 |
| WO | WO 2003068942 | 8/2003 |
| WO | WO 2003093295 | 11/2003 |
| WO | WO 2005054279 | 6/2005 |
| WO | WO 2011008823 | 1/2011 |

OTHER PUBLICATIONS

"Virtually." Merriam-Webster.com. Merriam-Webster, n.d. Web. Feb. 4, 2016, 1 page.

Abbott et al., "Astrocyte-endothelial interactions at the blood-brain barrier," *Nat Rev Neurosci.*, 7(1):41-53, Jan. 2006.

Abraham, "The factors that influence permeation across the blood-brain barrier," *Eur J Med Chem.*, 39(3):235-240, Mar. 2004.

Addgene vestor database, "Plasmid: pET-16b." Retrieved from the Internet: <URL: http://www.addgene.org/vector-database/2544/>. Retrieved on Jan. 28, 2014, 3 pages.

Agrelo, "A new molecular model of cellular aging based on werner syndrome," *Elsevier*, 68:770-780, Sep. 8, 2006.

Ansel, "Introduction to Pharmaceutical Dosage Forms," Fourth Edition 126, 1985.

Bacher et al., "Peripheral and central biodistribution of (111)In-labeled anti-beta-amyloid autoantibodies in a transgenic mouse model of Alzheimer's disease," *Neurosci Lett.*, 449(3):240-245, Jan. 16, 2009.

Ballantyne, "Peptide YY(1-36) and peptide YY(3-36): Part I. Distribution, release and actions," *Obes Surg.*, 16(5):651-658, May 2006.

(Continued)

*Primary Examiner* — Adam M Weidner

(74) *Attorney, Agent, or Firm* — Fish & Richardson P.C.

(57) ABSTRACT

Provided herein are materials and methods for delivering immunoglobulins (e.g. therapeutic immunoglobulins) across the blood-brain barrier.

17 Claims, 3 Drawing Sheets

Specification includes a Sequence Listing.

(56) References Cited

OTHER PUBLICATIONS

Barbetta et al., "A new model of Theiler's murine encephalomyelitis virus infection," [Poster], Mayo SURF symposium, 1 page, Aug. 2014.
Bass, "RNA interference. The short answer." Nature, 411(6836):428-429, May 24, 2001.
Blanchette and Fortin, "Blood-brain barrier disruption in the treatment of brain tumors," Methods Mol Biol., 686:447-463, 2011.
Boado et al., "Drug targeting of erythropoietin across the primate blood-brain barrier with an IgG molecular Trojan horse," J Pharmacol Exp Ther., 333(3):961-969, Epub. Mar. 16, 2010.
Bovi et al., "An Oncogene Isolated by Transfection of Kaposi's Sarcoma DNA Encodes a Growth Factor That Is a Member of the FGF Family," Cell, 50:729-737, 1987.
Brandon et al., "Mitochondrial mutations in cancer," Oncogene, 25:4647-4662, 2006.
Brown and Goldstein, "A receptor-mediated pathway for cholesterol homeostasis," Science, 232(4746):34-47, Apr. 4, 1986.
Casillas et al., "Transcriptional control of the DNA methyltransferases is altered in aging and neoplastically-transformed human fibroblasts," Mol Cell Biochem., 252(1-2):33-43, Oct. 2003.
Chen et al., "Transdermal protein delivery by a coadministered peptide identified via phage display," Nature Biotechnology, 24:455-460, 2006.
Chenna et al., "Multiple sequence alignment with the Clustal series of programs," Nucleic Acids Res., 31(13):3497-3500, Jul. 1, 2003.
Chinnery et al., "Peptide nucleic acid delivery to human mitochondria," Gene Ther., 1999, 6(12)1919-1928, Corrigendum: Gene Ther., 7:813, 2000.
Choi et al., "Microbubble-size dependence of focused ultrasound-induced blood-brain barrier opening in mice in vivo," IEEE Trans Biomed Eng., 57(1):145-154, Epub Oct. 20, 2009.
Cortazar et al., "Embryonic lethal phenotype reveals a function of TDG in maintaining epigenetic stability," Macmillan, 470:419-425, 2011.
Cosolo et al., "Blood-brain barrier disruption using mannitol: time course and electron microscopy studies," Am J Physiol., 256(2 Pt 2):R443-R447, Feb. 1989.
De Boer and Breimer, "The blood-brain barrier: clinical implications for drug delivery to the brain," J R Coll Physicians Lond, 28(6):502-506, Nov.-Dec. 1994.
Deane et al., "IgG-assisted age-dependent clearance of Alzheimer's amyloid beta peptide by the blood-brain barrier neonatal Fc receptor," J. Neurosci., 25:11495-11503, Dec. 14, 2005.
Deb et al., "CD8+ T cells cause disability and axon loss in a mouse model of multiple sclerosis," PLoS One., 5(8):e12478, Aug. 30, 2010.
Deb et al., "Functional characterization of mouse spinal cord infiltrating CD8+ lymphocytes," J Neuroimmunol., 214(1-2):33-42, Epub Jul. 10, 2009.
Deeken and Löscher, "The blood-brain barrier and cancer: transporters, treatment, and Trojan horses," Clin Cancer Res., 13(6):1663-1674, Mar. 15, 2007.
Deng, "Targeted drug delivery across the blood-brain barrier using ultrasound technique," Ther Deliv., 1(6):819-848, Dec. 2010.
Denora et al., "Recent advances in medicinal chemistry and pharmaceutical technology—strategies for drug delivery to the brain," Curr Top Med Chem, 9(2):182-196, 2009.
Deshayes et al., "Cell-penetrating peptides: tools for intracellular delivery of therapeutics," Cell. Mol. Life Sci., 62:1839-1849, 2005.
Deshayes et al., "On the mechanism of non-endosomal peptide-mediated cellular delivery of nucleic acids," Biochim Biophys Acta, 1667:141-147, 2004.
Dietz and Bähr, "Delivery of bioactive molecules into the cell: the Trojan horse approach," Mol Cell Neurosci., 27(2):85-131, Oct. 2004.
Dingwall and Laskey, "Nuclear targeting sequences—a consensus?" Trends Biochem Sci., 16(12):478-481, 1991.
Dokka et al., "Cellular Delivery of Oligonucleotides by Synthetic Import Peptide Carrier," Pharmaceutical Research, 14(12):1759-1764, 1997.
D'Souza et al., "DQAsome-mediated delivery of plasmid DNA toward mitochondria in living cells," J Control Release, 92:189-197, 2003.
Egholm et al., "PNA hybridizes to complementary oligonucleotides obeying the Watson-Crick hydrogen-bonding rules," Nature, 365(6446):566-568, Oct. 7, 1993.
Egleton and Davis, "Bioavailability and transport of peptides and peptide drugs into the brain," Peptides, 18(9):1431-1439, 1997.
Elbashir et al., "Duplexes of 21-nucleotide RNAs mediate RNA interference in cultured mammalian cells," Nature, 411(6836):494-498, May 24, 2001.
Ellison et al., "Evidence of Genetic Locus Heterogeneity for Familial Bicuspid Aortic Valve," J Surgical Research, 142:28-31, 2007.
Fagan et al., "Apolipoprotein E-containing high density lipoprotein promotes neurite outgrowth and is a ligand for the low density lipoprotein receptor-related protein," J Biol Chem., 271(47):30121-30125, Nov. 22, 1996.
Fan et al., "MTSS1, a novel target of DNA methyltransferase 3B, functions as a tumor suppressor in hepatocellular carcinoma," Macmillan, 31:2298-2308, 2012.
Ford et al., "Protein transduction: an alternative to genetic intervention?" Gene Ther., 8:1-4, 2001.
Friden et al., "Blood-brain barrier penetration and in vivo activity of an NGF conjugate," Science, 259(5093):373-377, Jan. 15, 1993.
Futaki et al., "Arginine-rich peptides: An abundant source of membrane-permeable peptides having potential as carriers for intracellular protein delivery," J. Biol. Chem., 276:5836-5840, 2001.
Galanis et al., "Duplication of leader sequence for protein targeting to mitochondira leads to increased import efficiency," FEBS Letters, 282(2):425-430, May 1991.
Garg et al., "Mutations in NOTCH1 cause aortic valve disease," Nature Pub Group, 437(8):270-274, 2005.
Goldstein and Betz, "The blood-brain barrier," Sci Am., 255(3):74-83, Sep. 1986.
Golubnitschaja, "Cell cycle checkpoints: the role and evaluation for early diagnosis of senescence, cardiovascular, cancer, and neurodegenerative diseases," Amino Acids, 32:359-371, Nov. 30, 2006.
Greig et al., "Pharmacokinetics of chlorambucil-tertiary butyl ester, a lipophilic chlorambucil derivative that achieves and maintains high concentrations in brain," Cancer Chemother Pharmacol., 25(5):320-325, 1990.
Gros et al., "A non-covalent peptide-based strategy for protein and peptide nucleic acid transduction," Biochimica et Biophysica Acta, 1758:384-393, 2006.
Hawkins and Davis, "The blood-brain barrier/neurovascular unit in health and disease," Pharmacol Rev., 57(2):173-185, Jun. 2005.
Hdeib and Sloan, "Convection-enhanced delivery of 131I-chTNT-1/B mAB for treatment of high-grade adult gliomas," Expert Opin Biol Ther., 11(6):799-806. Epub Apr. 27, 2011.
Hervé et al., "CNS delivery via adsorptive transcytosis," AAPS J., 10(3):455-472, Epub Aug. 26, 2008.
Hoey and Smith, "Chemistry of X-ray Constrast Media," Radiocontrast Agents, Sovak, ed. vol. 73 pp. 23-125 (1984).
Holcomb et al., "Accelerated Alzheimer-type phenotype in transgenic mice carrying both mutant amyloid precursor protein and presenilin 1 transgenes," Nat Med., 4(1):97-100, Jan. 1998.
Howe et al., "Hippocampal protection in mice with an attenuated inflammatory monocyte response to acute CNS picornavirus infection," Sci Rep., 2:545, Epub Jul. 30, 2012, 12 pages.
Hülsermann et al., "Uptake of apolipoprotein E fragment coupled liposomes by cultured brain microvessel endothelial cells and intact brain capillaries," J Drug Target, 17(8):610-618, Sep. 2009.
Hussain et al., "The mammalian low-density lipoprotein receptor family," Annu Rev Nutr., 19:141-172, 1999.
Hynynen et al., "Focal disruption of the blood-brain barrier due to 260-kHz ultrasound bursts: a method for molecular imaging and targeted drug delivery," J Neurosurg., 105(3):445-454, Sep. 2006.
Jefferies et al., "Transferrin receptor on endothelium of brain capillaries," Nature, 312:162-163, Nov. 8-14, 1984.

(56) References Cited

OTHER PUBLICATIONS

Joliot and Prochiantz, "Transduction peptides: from technology to physiology," Nature Cell Biol., 6(3):189-196, 2004.
Jurkowska et al., "Structure and Function of Mammalian DNA Methyltransferases," *Chem Bio Chem*, 12:206-222, 2011.
Karkan et al., "A unique carrier for delivery of therapeutic compounds beyond the blood-brain barrier," *PLoS One*, 3(6):e2469, Jun. 25, 2008.
Kim et al., "Translocation of poly(ethylene glycol-co-hexadecyl)cyanoacrylate nanoparticles into rate brain endothelial cells: role of apolipoproteins in receptor-mediated endocytosis," *Biomacromolecules*, 8(3):793-799, Mar. 2007.
Kioi et al., "Convection-enhanced delivery of interleukin-13 receptor-directed cytotoxin for malignant glioma therapy," *Technol Cancer Res Treat.*, 5(3):239-250, Jun. 2006.
Klein et al., "Mutations in DNMT1 cause hereditary sensory neuropathy with dementia and hearing loss," *Nature Henetics*, 43(6):595-602, Jun. 2011.
Kreuter et al., "Apolipoprotein-mediated transport of nanoparticle-bound drugs across the blood-brain barrier," *J Drug Target*, 10(4):317-325, Jun. 2002.
Leupold et al., "Apolipoprotein E peptide-modified colloidal carriers: The design determines the mechanism of uptake in vascular endothelial cells," *Biochim Biophys Acta*, 1788:442-449, 2009.
Lightowlers et al., "Mammalian mitochondrial genetics: heredity, heteroplasmy and disease," Trends Genet., 13(11):450-455, 1997.
Lin et al., "Inhibition of nuclear translocation of transcription factor NF-kappaB by a synthetic peptide containing a cell membrane-permeable motif and nuclear localization sequence," J. Biol. Chem., 70:14255-14258, 1995.
Mahlum et al., "Engineering a noncarrier to a highly efficient carrier peptide for noncovalently delivering biologically active proteins into human cells," *Anal Biochem.*, 365(2):215-221, Jun. 15, 2007.
Marquet et al., "Noninvasive, transient and selective blood-brain barrier opening in non-human primates in vivo," *PLoS One.*, 6(7):e22598, Epub Jul. 22, 2011.
Martín et al., "Design, synthesis and characterization of a new anionic cell-penetrating peptide: SAP(E)," *Chembiochem.*, 12(6):896-903, Epub Mar. 1, 2011.
Mazza et al., "Cancer and the blood-brain barrier: 'Trojan horses' for courses?" *Br J Pharmacol.*, 155(2):149-151, 2008.
Mesiwala et al., "High-intensity focused ultrasound selectively disrupts the blood-brain barrier in vivo," *Ultrasound Med Biol.*, 28(3):389-400, Mar. 2002.
Michaelis et al., "Covalent linkage of apolipoprotein e to albumin nanoparticles strongly enhances drug transport into the brain," *J Pharmacol Exp Ther.*, 317(3):1246-1253, Epub Mar. 22, 2006.
Misra et al., "Drug delivery to the central nervous system: a review," *J Pharm Pharm Sci.*, 6(2):252-273, 2003.
Morris et al., "A peptide carrier for the delivery of biologically active proteins into mammalian cells," *Nat Biotechnol*, 19(12):1173-1176, Dec. 2001.
Mousazadeh et al., "Gene delivery to brain cells with apoprotein E derived peptide conjugated to polylysine (apoEdp-PLL)," *J Drug Target.*, 15(3):226-230, Apr. 2007.
Padari et al., "Cell Transduction Pathways of Transportans," Bioconjugate Chem, 16:1399-1410, 2005.
Pan et al., "Efficient transfer of receptor-associated protein (RAP) across the blood-brain barrier," J Cell Sci., 117(Pt 21):5071-5078, Oct. 1, 2004.
Pardridge, "Blood-brain barrier delivery," Drug Discov Today, 12(1-2):54-61, Jan. 2007.
Pardridge, "Re-engineering biopharmaceuticals for delivery to brain with molecular Trojan horses," *Bioconjug Chem.*, 19(7):1327-38. Epub Jun. 12, 2008.
Patel et al., "Getting into the brain: approaches to enhance brain drug delivery," CNS Drugs, 2009, 23(1):35-58.
Persidsky et al., "Blood-brain barrier: structural components and function under physiologic and pathologic conditions," *J Neuroimmune Pharmacol.*, 1(3):223-236, Sep. 2006.
Poduslo et al., "Permeability of proteins at the blood-brain barrier in the normal adult mouse and double transgenic mouse model of Alzheimer's disease," *Neurobiol Dis.*, 8(4):555-567, Aug. 2001.
Prochiantz, "Messenger proteins: homeoproteins, TAT and others," Curr. Opin. Cell Biol., 12:400-406, 2000.
Rall et al., "Structural basis for receptor binding heterogeneity of apolipoprotein E from type III hyperlipoproteinemic subjects," *Proc. Natl. Acad. Sci. USA*, 79(15): 4696-4700, Aug. 1982.
Ramakrishnan et al., "Surface plasmon resonance binding kinetics of Alzheimer's disease amyloid beta peptide-capturing and plaque-binding monoclonal antibodies," *Biochemistry*, 48(43):10405-10415, Nov. 3, 2009.
Rayudu, *Radiotracers for Medical Applications*, vol. 1, pp. 201, Apr. 6, 1983.
Reese and Karnovsky, "Fine structural localization of a blood-brain barrier to exogenous peroxidase," *J Cell Biol.*, 34(1):207-217, Jul. 1967.
Rojas et al., "Genetic engineering of proteins with cell membrane permeability," Nature Biotechnology, 16:370-375, 1998.
Ruan et al., "Cytokine regulation of low-density lipoprotein receptor gene transcription in human mesangial cells," *Nephrol Dial Transplant.*, 13(6):1391-1397, Jun. 1998.
Ryser et al., "Histones and basic polyamino acids stimulate the uptake of albumin by tumor cells in culture," Science, 150:501-503, 1965.
Ryser, "A membrane effect of basic polymers dependent on molecular size," Nature, 215:934-936, 1967.
Ryser, "Transport of Macromolecules, Especially Proteins into Mammalian Cells," Proceedings of the Fourth International Congress of Pharmacology, 3:96-132, 1970.
Ryser, "Uptake of Protein by Mammalian Cells: An Underdeveloped Area," Science, 159:390-396, 1968.
Sarkar et al. "A carrier for non-covalent delivery of functional beta-galactosidase and antibodies against amyloid plaques and IgM to the brain," *PLOS One*, 6(12):e28881, Epub Dec. 21, 2011.
Sauer et al., "An apolipoprotein E-derived peptide mediates uptake of sterically stabilized liposomes into brain capillary endothelial cells," *Biochemistry*, 44(6):2021-2029, Feb. 15, 2005.
Scheld, "Drug delivery to the central nervous system: general principles and relevance to therapy for infections of the central nervous system," *Rev Infect Dis.*, 11 Suppl 7:S1669-S1690, Nov.-Dec. 1989.
Schwarze et al., "In vivo protein transduction: delivery of a biologically active protein into the mouse," *Science*, 285(5433):1569-1572, Sep. 3, 1999.
Seibel et al., "Transfection of mitochondria: strategy towards a gene therapy of mitochondrial DNA diseases," Nucleic Acids Res., 23(1):10-17, Jan. 1995.
Shamenkov et al., "Effects of apolipoproteins on dalargin transport across the blood-brain barrier," *Bull Exp Biol Med.*, 142(6):703-706, Dec. 2006.
Sheikov et al., "Cellular mechanisms of the blood-brain barrier opening induced by ultrasound in presence of microbubbles," *Ultrasound Med Biol.*, 30(7):979-989, Jul. 2004.
Shen and Ryser, "Conjugation of poly-L-lysine to albumin and horseradish peroxidase: A novel method of enhancing the cellular uptake of proteins," Proc. Natl. Acad. Sci. USA, 75:1872-1876, 1978.
Simeoni et al., "Insight into the mechanism of the peptide-based gene delivery system MPG: implications for delivery of siRNA into mammalian cells," Nucleic Acids Research, vol. 31(11):2717-2724, 2003.
Smith et al., "Strategies for treating disorders of the mitochondrial genome," Biochim Biophys Acta, 1659:232-239, 2004.
Spencer and Verma, "Targeted delivery of proteins across the blood-brain barrier," *Proc Natl Acad Sci U S A.*, 104(18):7594-7599, Epub Apr. 26, 2007.
Stein and Cheng, "Antisense oligonucleotides as therapeutic agents—is the bullet really magical?" *Science*, 261(5124):1004-1012, Aug. 20, 1993.
Tyler et al., "In vivo enhancement of ultrasonic image luminance by aqueous solutions with high speed of sound," *Ultrasonic Imaging*, 3, pp. 323-329, 1981.

(56) References Cited

OTHER PUBLICATIONS

UniProt Accession P02649, "APOE_HUMAN." Last sequence update Jul. 21, 1986, 16 pages.
van de Waterbeemd, "Estimation of blood-brain barrier crossing of drugs using molecular size and shape, and H-bonding descriptors," *J Drug Target*., 6(2):151-165, 1998.
Vuilleumier et al., "Autoantibodies to apolipoprotein A-1 as a biomarker of cardiovascular autoimmunity," *World J Cardiol*., 6(5):314-326, May 26, 2014.
Waterhouse, "Determination of lipophilicity and its use as a predictor of blood-brain barrier penetration of molecular imaging agents," *Mol Imaging Biol*., 5(6):376-389, Nov.-Dec. 2003.
Weiss et al., "The blood-brain barrier in brain homeostasis and neurological diseases," *Biochim Biophys Acta*, 1788(4):842-857, Apr. 2009.
Wender et al., "The design, synthesis, and evaluation of molecules that enable or enhance cellular uptake: Peptoid molecular transporters," Proc. Natl. Acad. Sci. USA, 97:13003-13008, 2000.
Wengenack et al., "Targeting alzhe mer amyloid plaques in vivo," *Nat Biotechnol*, 18(8):868-872, Aug. 2000.
Yang et al., "Binding site on human immunoglobulin G for the affinity ligand HWRGWV," *J Mol Recognit*., 23(3):271-282, May-Jun. 2010.
Zensi et al., "Albumin nanoparticles targeted with Apo E enter the CNS by transcytosis and are delivered to neurones," *J Control Release*., 137(1):78-86, Epub Mar. 11, 2009.
Zhao et al., "Chemical engineering of cell penetrating antibodies," J. Immunol. Meth., 254:137-145, 2001.
Zlokovic et al., "Differential regulation of leptin transport by the choroid plexus and blood-brain barrier and high affinity transport systems for entry into hypothalamus and across the blood-cerebrospinal fluid barrier," *Endocrinology*, 141:1434-1441, Apr. 2000.
Zlokovic, "The blood-brain barrier in health and chronic neurodegenerative disorders," *Neuron*, 57(2):178-201, Jan. 24, 2008.

* cited by examiner

PEPTIDE-MEDIATED DELIVERY OF IMMUNOGLOBULINS ACROSS THE BLOOD-BRAIN BARRIER

CROSS-REFERENCE TO RELATED APPLICATIONS

This application claims the benefit of U.S. Provisional Application Ser. No. 62/209,052, filed Aug. 24, 2015. The disclosure of the prior application is considered part of (and is incorporated by reference in) the disclosure of this application.

SEQUENCE LISTING

This application includes a sequence listing which has been submitted in electronic format. The ASCII text file, which is incorporated-by-reference herein, is titled "07039-1475001_SL.txt," was created on Sep. 26, 2016, and is 24,568 bytes in size.

TECHNICAL FIELD

This disclosure relates to materials and methods for delivering immunoglobulins across the blood-brain barrier.

BACKGROUND

The blood-brain barrier (BBB) prevents most macromolecules (e.g., DNA, RNA, and polypeptides) and many small molecules from entering the brain. The BBB is principally composed of specialized endothelial cells with highly restrictive tight junctions, consequently, passage of substances, small and large, from the blood into the central nervous system is controlled by the BBB. This structure makes treatment and management of patients with neurological diseases and disorders (e.g., brain cancer and Alzheimer's disease) difficult as many therapeutic agents cannot be delivered across the BBB with desirable efficiency.

SUMMARY

Provided herein are materials and methods for delivering immunoglobulins (e.g. therapeutic immunoglobulins) across the blood-brain barrier.

There are numerous potential therapeutic antibodies directed against brain cancers and other neurological disorders involving the brain. Provided herein are peptides that specifically binds to an immunoglobulin (e.g., a therapeutic immunoglobulin) and interacts with the low-density lipoprotein receptor (LDLR) present on the surface of endothelial cells of the blood-brain barrier (BBB). The peptides provided herein thus can bind an immunoglobulin and deliver it to the brain. The peptides can also create transient openings in the BBB, through which small molecules (e.g., imaging agents or therapeutic agents) can be transported to the brain.

In some embodiments, peptides provided herein can include the sequence $A_p$-$L_n$-$B_m$ (SEQ ID NO:1) where A is an immunoglobulin affinity ligand, L is a linker, and B is a blood-brain barrier agent including the sequence L-R-X1-R-X2-X3-X4-H-L-R-X5-X6-X7-K-R-L-X8-R-D-X9 (SEQ ID NO:3); where X1 is selected from the group consisting of A, L, S, and V; X2 is selected from the group consisting of L and M; X3 is selected from the group consisting of A and S; X4 is selected from the group consisting of N, S, and T;

X5 is selected from the group consisting of K and N; X6 is selected from the group consisting of L, M, and V; X7 is selected from the group consisting of R and P; X8 is selected from the group consisting of L and M; X9 is selected from the group consisting of A and L; n is an integer from 0 to 50 (e.g., 4); m is an integer from 1 to 3; and p is an integer from 1 to 4 (e.g., 1).

The immunoglobulin affinity ligand can include the sequence H-X10-X11-X12-X13-X14 (SEQ ID NO:25), wherein X10 is selected from the group consisting of W, Y, and F; X11 is selected from the group consisting of R and F; X12 is selected from the group consisting of K, and R; X13 is selected from the group consisting of W, F, and H; and X14 is selected from the group consisting of Z, V, D, and L; e.g., the sequence H-W-R-G-W-Z (SEQ ID NO:26). The immunoglobulin affinity ligand can non-covalently bind a therapeutic immunoglobulin. In some aspects, the therapeutic immunoglobulin can be an IgG immunoglobulin.

The linker can be selected from the group consisting of one or more hydrophilic amino acids, one or more neutral amino acids, and one or more amino acid analogs (e.g., one or more hydrophilic or neutral amino acid analogs). In some aspects, the linker is one or more hydrophilic amino acids (e.g., lysine).

The blood-brain barrier agent can include a sequence having at least 80% sequence identity to L-R-V-R-L-A-S-H-L-R-K-L-R-K-R-L-L-R-D-A (SEQ ID NO:4). For example, the blood-brain barrier agent can be L-R-V-R-L-A-S-H-L-R-K-L-R-K-R-L-L-R-D-A (SEQ ID NO:4).

In some embodiments, peptides provided herein can include the sequence $A_p$-$L_n$-$B_m$ (SEQ ID NO:1) wherein A is an immunoglobulin affinity ligand, where A includes the sequence H-W-R-G-W-Z (SEQ ID NO:26) and p is 1; L is a linker, where L is a lysine and n is 4; and B is a blood-brain barrier agent, where B includes the sequence L-R-V-R-L-A-S-H-L-R-K-L-R-K-R-L-L-R-D-A (SEQ ID NO:4) and m is an integer from 1 to 3.

In some embodiments, peptides provided herein are present in a complex. In some aspects a complex can include a peptide and a therapeutic immunoglobulin. The peptide can include the sequence $A_p$-$L_n$-$B_m$ (SEQ ID NO:1) wherein A is an immunoglobulin affinity ligand; L is a linker; and B is a blood-brain barrier agent including the sequence L-R-X1-R-X2-X3-X4-H-L-R-X5-X6-X7-K-R-L-X8-R-D-X9 (SEQ ID NO:3); wherein X1 is selected from the group consisting of A, L, S, and V; X2 is selected from the group consisting of L and M; X3 is selected from the group consisting of A and S; X4 is selected from the group consisting of N, S, and T; X5 is selected from the group consisting of K and N; X6 is selected from the group consisting of L, M, and V; X7 is selected from the group consisting of R and P; X8 is selected from the group consisting of L and M; X9 is selected from the group consisting of A and L; n is an integer from 0 to 50 (e.g., 4); m is an integer from 1 to 3; and p is an integer from 1 to 4 (e.g., 1).

The immunoglobulin affinity ligand can include the sequence H-X10-X11-X12-X13-X14 (SEQ ID NO:25); wherein X10 is selected from the group consisting of W, Y, and F; X11 is selected from the group consisting of R and F; X12 is selected from the group consisting of K, and R; X13 is selected from the group consisting of W, F, and H; and X14 is selected from the group consisting of Z, V, D, and L. In some aspects, the immunoglobulin affinity ligand can be H-W-R-G-W-Z (SEQ ID NO:26). The immunoglobulin affinity ligand can be non-covalently bound to the therapeutic immunoglobulin. In some aspects, the therapeutic immunoglobulin can be an IgG immunoglobulin.

The linker can be selected from the group consisting of one or more hydrophilic amino acids, one or more neutral amino acids, and one or more amino acid analogs (e.g., one or more hydrophilic or neutral amino acid analogs). In some aspects, the linker can be one or more hydrophilic amino acids (e.g., lysine).

The blood-brain barrier agent can include a sequence having at least 80% sequence identity to L-R-V-R-L-A-S-H-L-R-K-L-R-K-R-L-L-R-D-A (SEQ ID NO:4). In some aspects, the blood-brain barrier agent is L-R-V-R-L-A-S-H-L-R-K-L-R-K-R-L-L-R-D-A (SEQ ID NO:4).

The therapeutic immunoglobulin can be selected from the group consisting of cetuximab, bococizumab, dinutuximab, racotumomab, ralpancizumab, and avastin. In some aspects, the therapeutic immunoglobulin is cetuximab.

In some aspects, a complex can include a peptide and a therapeutic immunoglobulin. The peptide can include the sequence H-W-R-G-W-Z-K-K-K-K-L-R-X1-R-X2-X3-X4-H-L-R-X5-X6-X7-K-R-L-X8-R-D-X9 (SEQ ID NO: 43); wherein X1 is selected from the group consisting of A, L, S, and V; X2 is selected from the group consisting of L and M; X3 is selected from the group consisting of A and S; X4 is selected from the group consisting of N, S, and T; X5 is selected from the group consisting of K and N; X6 is selected from the group consisting of L, M, and V; X7 is selected from the group consisting of R and P; X8 is selected from the group consisting of L and M; X9 is selected from the group consisting of A and L. In some embodiments, the therapeutic immunoglobulin is cetuximab.

In some aspects, a complex can include a peptide and a therapeutic immunoglobulin, the peptide including the sequence H-W-R-G-W-Z-K-K-K-K-L-R-V-R-L-A-S-H-L-R-K-L-R-K-R-L-L-R-D-A (SEQ ID NO:42).

Also provided herein are methods. For example, included herein are methods of transporting a therapeutic immunoglobulin across the blood-brain barrier of a patient, and methods of treating a neurological disorder in a patient. In some embodiments, the methods can include administering to the patient an effective amount of a peptide and administering to the patient an effective amount of a therapeutic immunoglobulin. The peptide can include the sequence $A_p$-$L_n$-$B_m$ (SEQ ID NO:1) where A is an immunoglobulin affinity ligand; L is a linker; and B is a blood-brain barrier agent including the sequence L-R-X1-R-X2-X3-X4-H-L-R-X5-X6-X7-K-R-L-X8-R-D-X9 (SEQ ID NO:3); where X1 is selected from the group consisting of A, L, S, and V; X2 is selected from the group consisting of L and M; X3 is selected from the group consisting of A and S; X4 is selected from the group consisting of N, S, and T; X5 is selected from the group consisting of K and N; X6 is selected from the group consisting of L, M, and V; X7 is selected from the group consisting of R and P; X8 is selected from the group consisting of L and M; X9 is selected from the group consisting of A and L; n can be an integer from 0 to 50 (e.g., 4); m can be an integer from 1 to 3; and p can be an integer from 1 to 4 (e.g., 1).

The immunoglobulin affinity ligand can include the sequence H-X10-X11-X12-X13-X14 (SEQ ID NO:25), wherein X10 is selected from the group consisting of W, Y, and F; X11 is selected from the group consisting of R and F; X12 is selected from the group consisting of K, and R; X13 is selected from the group consisting of W, F, and H; and X14 is selected from the group consisting of Z, V, D, and L. In some aspects, the immunoglobulin affinity ligand can be H-W-R-G-W-Z (SEQ ID NO:26). The immunoglobulin affinity ligand can non-covalently bind the therapeutic immunoglobulin. In some aspects, the therapeutic immunoglobulin can be an IgG immunoglobulin.

The linker can be selected from the group consisting of one or more hydrophilic amino acids, one or more neutral amino acids, and one or more amino acid analogs (e.g., one or more hydrophilic or neutral amino acid analogs). In some aspects, the linker is one or more hydrophilic amino acids (e.g., lysine).

The blood-brain barrier agent can include a sequence having at least 80% sequence identity to L-R-V-R-L-A-S-H-L-R-K-L-R-K-R-L-L-R-D-A (SEQ ID NO:4). For example, the blood-brain barrier agent can be L-R-V-R-L-A-S-H-L-R-K-L-R-K-R-L-L-R-D-A (SEQ ID NO:4).

The therapeutic immunoglobulin can be selected from the group consisting of cetuximab, bococizumab, dinutuximab, racotumomab, ralpancizumab, and avastin. In some aspects, the therapeutic immunoglobulin is cetuximab.

The peptide and the therapeutic immunoglobulin can be admixed prior to administering to the patient.

The neurological disorder can be selected from meningitis, epilepsy, multiple sclerosis, neuromyelitis optica, late-stage neurological trypanosomiasis, Parkinson's, progressive multifocal leukoencephalopathy, De Vivo disease, Alzheimer's disease, HIV Encephalitis, addiction, and cancer.

The methods can include administering to the patient an additional active agent. The additional active agent can be administered about 5 minutes to about 2 hours after the peptide. In some aspects, the additional active agent can be an imaging agent (e.g., one or more of a radionuclide, a paramagnetic metal, a fluorochrome, a dye, and an enzyme substrate). In some aspects, the additional active agent can be a therapeutic agent (e.g., a polypeptide, an oligonucleotide, an antibiotic, an antiviral agent, a cancer drug (e.g., ZD6474 and INCB3619), an anti-addiction drug, and an anesthetic).

Unless otherwise defined, all technical and scientific terms used herein have the same meaning as commonly understood by one of ordinary skill in the art to which this disclosure belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
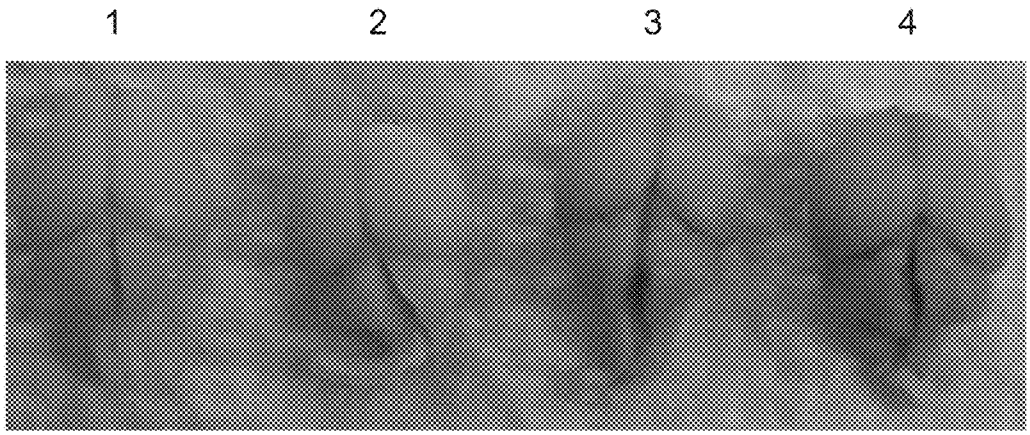
FIG. 1 shows the results of transportation of Evan's Blue (EB) across the BBB using various amounts of peptide and administration techniques. 1) EB only; 2) 300 μg Apo-I peptide followed by EB; 3) 600 μg Apo-I peptide followed by EB; 4) 600 μg Apo-I peptide+200 μg cetuximab, followed by EB.

Provided herein are materials and methods for transporting an immunoglobulin (e.g., a therapeutic immunoglobulin) across the blood-brain barrier (BBB) in a patient. For example, the methods provided herein can be used to treat a brain disease in a patient, such as brain cancer.

Provided herein are peptides having a first moiety including an immunoglobulin affinity ligand and a second moiety including a blood-brain barrier agent. The immunoglobulin affinity ligand can be covalently bound at either or both termini of the blood-brain barrier agent. For example, the immunoglobulin affinity ligand can be present at the N-terminus of the blood-brain barrier agent or the immunoglobulin affinity ligand can be present at the C-terminus of the blood-brain barrier agent. The first and second moieties can be connected by a linker.

In some embodiments, a peptide provided herein has the following sequence:

(SEQ ID NO: 1)
$A_p$-$L_n$-$B_m$.

In some embodiments, a peptide provided herein has the following sequence:

(SEQ ID NO: 2)
$B_m$-$L_n$-$A_p$.

The variable A is an immunoglobulin affinity ligand. The variable L is a linker. The variable B is a blood-brain barrier agent. The variable m is an integer from 1 to 3. For example, m can be 1, 2, or 3. In some embodiments, m is 1. The variable p is an integer from 1 to 4. For example, p can be 1, 2, 3, or 4. In some embodiments, p is 1. The variable n is an integer ranging from 0 to 50 (e.g., 4, 6, 8, 10, 12, 16, 20, 24, 26, 28, 32, 36, 40, 42, 44, 48, and 50). For example, n can range from 4 to 20, from 8 to 16, or from 10 to 12. In some embodiments, n is chosen from 4, 8, 12, 16, and 20. For example, n can be 16. In some embodiments, n is 4.

Blood-Brain Barrier Agent

Peptides provided herein include a blood brain barrier agent (B). A blood-brain barrier agent, as used herein, is any polypeptide or non-polypeptide ligand that can open the blood-brain barrier such that a target compound can cross the blood-brain barrier. Blood brain barrier agents have been described, for example, in Curran et al., US 2012/107243, and Sarkar et al., US 2014/0314663, each of which is incorporated by reference herein.

In some embodiments, a blood-brain barrier agent has a cognate receptor on brain cells or can bind to such receptors. In some embodiments, the blood-brain barrier agent includes a transferrin-receptor binding site of a transferrin. In some embodiments, the blood-brain barrier agent includes a receptor binding domain of an apolipoprotein. A receptor binding domain of an apolipoprotein (Apo), for example, can be chosen from the receptor binding domain of ApoA, ApoB, ApoC, ApoD, ApoE, ApoE2, ApoE3, ApoE4, and fragments and combinations thereof. In some embodiments, the receptor binding domain of an apolipoprotein is chosen from the receptor binding domain of ApoB and ApoE. In some embodiments, the receptor binding domain of an apolipoprotein is the receptor binding domain of ApoE.

In some embodiments, the blood-brain barrier agent includes a sequence having at least 80% (e.g., at least 85%; at least 90%; at least 92%; at least 95%; at least 98%; and at least 99%) sequence identity to: L-R-V-R-L-A-S-H-L-R-K-L-R-K-R-L-L-R-D-A (SEQ ID NO:4).

In some embodiments, the blood-brain barrier agent includes a polypeptide having at least 80% (e.g., at least 85%; at least 90%; at least 92%; at least 95%; at least 98%; or at least 99%) sequence identity to the sequence L-R-X1-R-X2-X3-X4-H-L-R-X5-X6-X7-K-R-L-X8-R-D-X9 (SEQ ID NO:3), wherein:

X1 is selected from the group consisting of A, L, S, and V;
X2 is selected from the group consisting of L and M;
X3 is selected from the group consisting of A and S;
X4 is selected from the group consisting of N, S, and T;
X5 is selected from the group consisting of K and N;
X6 is selected from the group consisting of L, M, and V;
X7 is selected from the group consisting of R and P;
X8 is selected from the group consisting of L and M; and
X9 is selected from the group consisting of A and L.

Non-limiting examples of a blood-brain barrier agents according to this sequence include:

(SEQ ID NO: 4)
L-R-V-R-L-A-S-H-L-R-K-L-R-K-R-L-L-R-D-A;

(SEQ ID NO: 5)
L-R-S-R-L-A-S-H-L-R-K-L-R-K-R-L-L-R-D-A;

(SEQ ID NO: 6)
L-R-V-R-M-A-S-H-L-R-K-L-R-K-R-L-L-R-D-A;

(SEQ ID NO: 7)
L-R-V-R-L-A-T-H-L-R-K-L-R-K-R-L-L-R-D-A;

(SEQ ID NO: 8)
L-R-V-R-L-A-S-H-L-R-K-L-P-K-R-L-L-R-D-A;

(SEQ ID NO: 9)
L-R-V-R-L-A-S-H-L-R-K-L-R-K-R-L-M-R-D-A;

(SEQ ID NO: 10)
L-R-V-R-L-A-S-H-L-R-N-L-R-K-R-L-L-R-D-A;

(SEQ ID NO: 11)
L-R-V-R-L-A-S-H-L-R-K-V-R-K-R-L-L-R-D-A;

(SEQ ID NO: 12)
L-R-V-R-M-S-S-H-L-R-K-L-R-K-R-L-L-R-D-A;

(SEQ ID NO: 13)
L-R-V-R-L-A-S-H-L-R-N-V-R-K-R-L-L-R-D-A;

(SEQ ID NO: 14)
L-R-V-R-L-A-S-H-L-R-N-M-R-K-R-L-L-R-D-A;

(SEQ ID NO: 15)
L-R-A-R-M-A-S-H-L-R-K-L-R-K-R-L-L-R-D-A;

(SEQ ID NO: 16)
L-R-V-R-L-S-S-H-L-R-K-L-R-K-R-L-M-R-D-A;

(SEQ ID NO: 17)
L-R-S-R-L-A-S-H-L-R-K-L-R-K-R-L-M-R-D-A;

-continued

```
                                (SEQ ID NO: 18)
L-R-V-R-L-S-S-H-L-P-K-L-R-K-R-L-L-R-D-A;

                                (SEQ ID NO: 19)
L-R-V-R-L-S-S-H-L-R-K-L-P-K-R-L-L-R-D-A;

                                (SEQ ID NO: 20)
L-R-V-R-L-A-S-H-L-R-K-M-R-K-R-L-M-R-D-A;

                                (SEQ ID NO: 21)
L-R-V-R-L-A-S-H-L-R-N-L-P-K-R-L-L-R-D-A;

                                (SEQ ID NO: 22)
L-R-L-R-L-A-N-H-L-R-K-L-R-K-R-L-L-R-D-A;

                                (SEQ ID NO: 23)
L-R-L-R-L-A-S-H-L-R-K-L-R-K-R-L-L-R-D-L;
and

                                (SEQ ID NO: 24)
L-R-V-R-L-A-N-H-L-R-K-L-R-K-R-L-L-R-D-L.
```

In some embodiments, the blood-brain barrier agent is less than 100 amino acids in length (e.g., less than 90 amino acids in length; less than 80 amino acids in length; less than 70 amino acids in length; less than 60 amino acids in length; less than 50 amino acids in length; less than 40 amino acids in length; less than 35 amino acids in length; less than 30 amino acids in length; less than 28 amino acids in length; and less than 25 amino acids in length). In some embodiments, the blood-brain barrier agent can range from 10 to 35 (e.g., 10, 12, 15, 17, 19, 20, 22, 25, 28, 31, 32, and 35) amino acids in length. For example, the blood-brain barrier agent can range from 15 to 25, from 18 to 26, or from 20 to 22 amino acids in length. In some embodiments, the blood-brain barrier agent is about 20 amino acids in length.

"Percent sequence identity" refers to the degree of sequence identity between any given reference sequence, e.g., L-R-V-R-L-A-S-H-L-R-K-L-R-K-R-L-L-R-D-A (SEQ ID NO:4), and a candidate blood-brain barrier agent sequence. A candidate sequence typically has a length that is from 80 percent to 200 percent of the length of the reference sequence (e.g., 82, 85, 87, 89, 90, 93, 95, 97, 99, 100, 105, 110, 115, 120, 130, 140, 150, 160, 170, 180, 190, and 200 percent of the length of the reference sequence). A percent identity for any candidate nucleic acid or polypeptide relative to a reference nucleic acid or polypeptide can be determined as follows. A reference sequence (e.g., a nucleic acid sequence or an amino acid sequence) is aligned to one or more candidate sequences using the computer program ClustalW (version 1.83, default parameters), which allows alignments of nucleic acid or polypeptide sequences to be carried out across their entire length (global alignment). Chenna et al., *Nucleic Acids Res.,* 31(13):3497-500 (2003).

ClustalW calculates the best match between a reference and one or more candidate sequences, and aligns them so that identities, similarities and differences can be determined. Gaps of one or more residues can be inserted into a reference sequence, a candidate sequence, or both, to maximize sequence alignments. For fast pairwise alignment of nucleic acid sequences, the following default parameters are used: word size: 2; window size: 4; scoring method: percentage; number of top diagonals: 4; and gap penalty: 5. For multiple alignment of nucleic acid sequences, the following parameters are used: gap opening penalty: 10; gap extension penalty: 5.0; and weight transitions: yes. For fast pairwise alignment of peptide sequences, the following parameters are used: word size: 1; window size: 5; scoring method: percentage; number of top diagonals: 5; gap penalty: 3. For multiple alignment of peptide sequences, the following parameters are used: weight matrix: blosum; gap opening penalty: 10; gap extension penalty: 0.5; hydrophilic gaps: on; hydrophilic residues: Gly, Pro, Ser, Asn, Asp, Gln, Glu, Arg, and Lys; residue-specific gap penalties: on. The ClustalW output is a sequence alignment that reflects the relationship between sequences. ClustalW can be run, for example, at the Baylor College of Medicine Search Launcher site (searchlauncher.bcm.tmc.edu/multi-align/multi-align.html) and at the European Bioinformatics Institute site on the World Wide Web (ebi.ac.uk/clustalw).

To determine percent identity of a candidate nucleic acid or amino acid sequence to a reference sequence, the sequences are aligned using ClustalW, the number of identical matches in the alignment is divided by the length of the reference sequence, and the result is multiplied by 100. It is noted that the percent identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

Linker

Peptides provided herein optionally include a linker (L). A linker (or spacer), as used herein, is any polypeptide or non-polypeptide used to join a blood-brain barrier agent and an immunoglobulin affinity peptide ligand.

In some embodiments, the linker includes one or more hydrophilic amino acids. As used herein, the term amino acids can include non-natural derivatives of amino acids. A hydrophilic amino acid can be chosen from: arginine, asparagine, aspartic acid, glutamic acid, glutamine, histidine, lysine, serine, threonine, tyrosine, and combinations and non-natural derivatives thereof. Non-natural derivatives of hydrophilic amino acids include, for example, histamine. In some embodiments, a hydrophilic amino acid can be chosen from lysine or a non-natural lysine derivative (e.g., DL-5-Hydroxylysine hydrochloride, Fmoc-Lys(palmitoyl)-OH, and Fmoc-β-Lys(Boc)-OH), arginine or a non-natural arginine derivative (e.g., L-2-Amino-3-guanidinopropionic acid hydrochloride, 4-Guanidinobutyric acid, and 3-Guanidinopropionic acid), and combinations thereof. In some embodiments, the hydrophilic amino acid is lysine. Non-limiting examples of a linker can include lysine (K), arginine (R), or any combination thereof (e.g., KR, KR, KKR, KRK, and RRK). Hydrophilic amino acid linkers have been described, for example, in Curran et al., US 2012/107243, and Sarkar et al., US 2014/0314663, each of which is incorporated by reference herein.

In some embodiments, the linker includes one or more neutral amino acids. A neutral amino acid can be chosen from: alanine, asparagine, cysteine, glutamine, glycine, isoleucine, leucine, methionine, phenylalanine, proline, serine, threonine, tryptophan, tyrosine, valine, and combinations and non-natural derivatives thereof.

In some embodiments, the linker includes one or more amino acid analogs. An amino acid analog can be chosen from: aminohexylacrylamide, aminoalkynyl, aminoethoxyethyl.

Affinity Ligand

Peptides provided herein include an immunoglobulin affinity ligand (A). An immunoglobulin affinity ligand, as used herein, is any polypeptide or non-polypeptide ligand that can bind with affinity to a specific immunoglobulin. In some embodiments, an immunoglobulin affinity ligand can be a polypeptide ligand. In some embodiments, an immunoglobulin affinity ligand can bind with high affinity to a specific immunoglobulin.

In some embodiments, the immunoglobulin affinity ligand is less than 12 amino acids in length (e.g., less than 11 amino acids in length; less than 10 amino acids in length; less than 9 amino acids in length; less than 8 amino acids in length; or less than 7 amino acids in length). In some embodiments, the immunoglobulin affinity ligand can range from 4 to 12 (e.g., 4, 5, 6, 7, 8, 9, 10, 11, or 12) amino acids in length. For example, the immunoglobulin affinity ligand can range from 5 to 10, or from 6 to 8 amino acids in length. In some embodiments, the immunoglobulin affinity ligand is about 6 amino acids in length.

In some embodiments, the immunoglobulin affinity ligand includes a sequence having at least 80% (e.g., at least 85%; at least 90%; at least 92%; at least 95%; at least 98%; or at least 99%) sequence identity to H-W-R-G-W-Z (SEQ ID NO:26). Percent sequence identity refers to the degree of sequence identity between any given reference sequence, e.g., H-W-R-G-W-Z (SEQ ID NO:26), and a candidate immunoglobulin affinity ligand. A candidate immunoglobulin affinity ligand sequence typically has a length that is from 80 percent to 200 percent of the length of the reference sequence (e.g., 82, 85, 87, 89, 90, 93, 95, 97, 99, 100, 105, 110, 115, 120, 130, 140, 150, 160, 170, 180, 190, and 200 percent of the length of the reference sequence). How to determine percent identity of a candidate nucleic acid or amino acid sequence to a reference sequence is as described elsewhere herein.

In some embodiments, the immunoglobulin affinity ligand includes a sequence having at least 80% (e.g., at least 85%; at least 90%; at least 92%; at least 95%; at least 98%; or at least 99%) sequence identity to the sequence H-X10-X11-X12-X13-X14 (SEQ ID NO:25), wherein:

X10 is selected from the group consisting of W, Y, and F;
X11 is selected from the group consisting of R and F;
X12 is selected from the group consisting of K, and R;
X13 is selected from the group consisting of W, F, and H; and
X14 is selected from the group consisting of Z, V, D, and L.

Non-limiting examples of an immunoglobulin affinity ligand according to this sequence include:

```
                              (SEQ ID NO: 26)
H-W-R-G-W-Z;

                              (SEQ ID NO: 27)
H-W-R-G-W-V;

                              (SEQ ID NO: 28)
H-W-R-G-W-V;

                              (SEQ ID NO: 29)
H-Y-F-K-F-D;
and

                              (SEQ ID NO: 30)
H-F-R-R-H-L.
```

In some embodiments, the immunoglobulin affinity ligand can include any peptide sequence which binds an immunoglobulin. Non-limiting examples of immunoglobulin affinity domains can include:

```
                              (SEQ ID NO: 31)
Q-N-A-F-Y-E-I-L;

                              (SEQ ID NO: 32)
Y-D-W-I-P-S-S-A-W;
```

-continued

```
                              (SEQ ID NO: 33)
A-G-A-I-W-Q-R-D-W;

                              (SEQ ID NO: 34)
S-W-I-S-S-R-D-W-T;

                              (SEQ ID NO: 35)
E-A-B-Y-S-K-D-W-L;

                              (SEQ ID NO: 36)
N-D-N-G-V-D-G-E-W-T-Y;

                              (SEQ ID NO: 37)
D-W-I-P-Q-A-S-W-E;

                              (SEQ ID NO: 38)
E-P-I-H-R-S-T-L-T-A-L-L;

                              (SEQ ID NO: 39)
G-F-R-K-Y-L-H-F-R-R-H-L-L;
and

                              (SEQ ID NO: 40)
V-R-L-G-W-L-L-A-P-A-D-L-D-A-R.
```

The affinity ligand can have affinity for any immunoglobulin isotype. For example, the affinity ligand can have affinity for an IgA, IgG IgD, IgE, or IgM immunoglobulin. In some embodiments, the immunoglobulin is an IgG immunoglobulin (e.g., SEQ ID NOs:25-30). In some embodiments, the immunoglobulin is an IgM immunoglobulin (e.g., SEQ ID NOs:32-35).

In some embodiments, the immunoglobulin affinity ligand binds the therapeutic immunoglobulin to be delivered across the BBB. The immunoglobulin affinity ligand can bind the therapeutic immunoglobulin through any chemical interaction. Typically, the immunoglobulin affinity ligand can bind the therapeutic immunoglobulin through a weak chemical interaction. For example, the immunoglobulin affinity ligand can bind the therapeutic immunoglobulin via non-covalent bonds, electrostatic interactions, hydrogen bonds, van der Waals forces, or hydrophobic interactions. In some embodiments, the immunoglobulin affinity ligand non-covalently binds the therapeutic immunoglobulin.

Immunoglobulins

The term "immunoglobulin" or "antibody" as used herein refers to immunoglobulin molecules and immunologically active portions of immunoglobulin molecules (i.e., molecules that contain an antigen binding site that specifically binds to a peptide). An immunoglobulin can be a monoclonal antibody, a polyclonal antibody, a humanized antibody, a fully human antibody, a single chain antibody, a chimeric antibody, or a fragment thereof. The term "fragment" of a full length immunoglobulin refers to one or more portions of a full-length immunoglobulin that retain the ability to specifically bind to a target of interest.

The immunoglobulin can be any isotype. For example, the immunoglobulin can be an IgA, IgG IgD, IgE, or IgM immunoglobulin. In some embodiments, the immunoglobulin is an IgG immunoglobulin.

The methods provided herein provide transport of an immunoglobulin across the BBB, in particular those with low blood-brain barrier permeability. In some embodiments, an immunoglobulin is an endogenous (e.g., originating from or native to a patient) immunoglobulin. In some embodiments, an immunoglobulin is an exogenous (e.g., originating from or synthesized outside of a patient) immunoglobulin.

In some embodiments, an immunoglobulin is a therapeutic immunoglobulin. Therapeutic immunoglobulins include, for example, approved and investigational therapeutic immunoglobulins. Therapeutic immunoglobulins approved by the U.S. Food and Drug Administration (FDA) can be viewed, for example, on the FDA website (fda.gov). Therapeutic immunoglobulins approved by the European Medicines Agency (EMA) can be viewed, for example, on the EMA website (ema.europa.eu). A therapeutic immunoglobulin can be a human antibody, a chimeric antibody, a humanized antibody, or a hybrid antibody. Therapeutic immunoglobulins can include, for example, cetuximab, bococizumab, dinutuximab, racotumomab, ralpancizumab, and avastin. In some embodiments, a therapeutic immunoglobulin is cetuximab.

Complex

Provided herein are complexes including a peptide described herein and an immunoglobulin described herein.

In some embodiments, a complex includes a peptide described herein and a therapeutic immunoglobulin. The therapeutic immunoglobulin can be an IgG immunoglobulin. The therapeutic immunoglobulin can be selected from cetuximab, bococizumab, dinutuximab, racotumomab, ralpancizumab, and avastin. In some embodiments, the therapeutic immunoglobulin is cetuximab.

In some embodiments, a complex includes a peptide comprising the sequence: H-X10-X11-X12-X13-X14-K-K-K-K-L-R-X1-R-X2-X3-X4-H-L-R-X5-X6-X7-K-R-L-X8-R-D-X9 (SEQ ID NO:41); wherein:

X1 is selected from the group consisting of A, L, S, and V;
X2 is selected from the group consisting of L and M;
X3 is selected from the group consisting of A and S;
X4 is selected from the group consisting of N, S, and T;
X5 is selected from the group consisting of K and N;
X6 is selected from the group consisting of L, M, and V;
X7 is selected from the group consisting of R and P;
X8 is selected from the group consisting of L and M;
X9 is selected from the group consisting of A and L;
X10 is selected from the group consisting of W, Y, and F;
X11 is selected from the group consisting of R and F;
X12 is selected from the group consisting of K, and R;
X13 is selected from the group consisting of W, F, and H; and
X14 is selected from the group consisting of Z, V, D, and L and a therapeutic immunoglobulin as provided herein. In some embodiments, the therapeutic immunoglobulin is cetuximab.

In some embodiments, a complex includes a peptide comprising the sequence: H-W-R-G-W-Z-K-K-K-K-L-R-V-R-L-A-S-H-L-R-K-L-R-K-R-L-L-R-D-A (SEQ ID NO:42), and a therapeutic immunoglobulin as provided herein. In some embodiments, the therapeutic immunoglobulin is cetuximab.

The peptide can bind to the immunoglobulin (via the immunoglobulin affinity ligand) through any chemical interaction. Typically, the bond is a weak chemical interaction. For example, the bond can be a non-covalent bond, an electrostatic interaction, a hydrogen bond, van der Waals force, or a hydrophobic interaction. In some embodiments, the peptide is non-covalently bound to the therapeutic immunoglobulin.

Methods of Use

Provided herein are methods of using a peptide described herein. For example, the methods provided herein can include administering a peptide as described herein to a patient. In some embodiments, this disclosure provides methods of transporting an immunoglobulin across the BBB of a patient. In some embodiments, this disclosure provides methods of transporting an active agent across the BBB of a patient. Transporting an immunoglobulin and/or an active agent across the BBB can include transcytosis of the immunoglobulin. In some embodiments, this disclosure provides methods of treating a neurological disorder in a patient. Methods provided herein can include administering a peptide as provided herein and, optionally, administering a therapeutic immunoglobulin as provided herein and/or an active agent as provided herein to the patient.

A patient can include both mammals and non-mammals. Mammals include, for example, humans; nonhuman primates, e.g. apes and monkeys; cattle; horses; sheep; rats; mice; pigs; and goats. Non-mammals include, for example, fish and birds.

In embodiments that include administering both a peptide as provided herein and administering a therapeutic immunoglobulin as provided herein, the peptide described herein and the therapeutic immunoglobulin can be administered to the patient independently or the therapeutic immunoglobulin can be admixed prior to administering to the patient. In some embodiments, the method includes contacting a peptide as described herein and an immunoglobulin under conditions allowing the peptide and the immunoglobulin to form a complex prior to administering to the patient. In some embodiments, the methods can include administering a complex including a peptide described herein and an immunoglobulin described herein.

In some embodiments, the neurological disorder is selected from: meningitis, epilepsy, multiple sclerosis, neuromyelitis optica, late-stage neurological trypanosomiasis, Parkinson's, progressive multifocal leukoencephalopathy, De Vivo disease, Alzheimer's disease, HIV Encephalitis, addiction, and cancer. For example, a neurological disorder can be a brain cancer, for example astrocytoma, medulloblastoma, glioma, ependymoma, germinoma (pinealoma), glioblastoma multiform, oligodendroglioma, schwannoma, retinoblastoma, and congenital tumors; or a cancer of the spinal cord, e.g., neurofibroma, meningioma, glioma, and sarcoma.

In some embodiments of methods provided herein, the administering of a peptide as provided herein to the patient can be followed by subsequent administration of an active agent.

In some embodiments, the active agent is an imaging agent. An imaging agent, as used herein, can be any chemical or substance which is used to provide a signal or contrast in imaging. The signal enhancing domain can be an organic molecule, metal ion, salt or chelate, particle (particularly iron particle), or labeled peptide, protein, polymer or liposome. For example, an imaging agent can include one or more of a radionuclide, a paramagnetic metal, a fluorochrome, a dye, and an enzyme substrate.

In some embodiments, the active agent is a therapeutic agent. As used herein, a therapeutic agent includes any molecule which, if transported across the BBB, can have a therapeutic effect. Examples of therapeutic agents include polypeptides (e.g., functional domains of biologically active molecules, growth factors, enzymes, transcription factors, toxins, antigenic peptides (as for vaccines), antibodies, and antibody fragments), oligonucleotides (e.g., natural or engineered plasmids, coding DNA sequences, antisense DNA sequences, mRNAs, antisense RNA sequences, RNAis, and siRNAs), a broad-spectrum antibiotic (e.g., cefotaxime, ceftriaxone, ampicillin and vancomycin); an antiviral agent (e.g., acyclovir), cancer drugs (e.g., daunorubicin, doxorubicin, bevacizumab, irinotecan, zoledronate, temozolomide, taxol, methotrexate, and cisplatin), anti-addiction drugs, and anesthetics. Further examples of therapeutic agents include, without limitation, acetazolamide, carbamazepine, clonazepam, clorazepate dipotassium, diazepam, divalproex sodium, ethosuximide, felbamate, fosphenytoin sodium, gabapentin, lamotrigine, levetiracetam, lorazepam, oxcarbazepine, phenobarbital, phenytoin, phenytoin sodium, pregabalin, primidone, tiagabine hydrochloride, topiramate, trimethadione, valproic acid, zonisamide, copaxone, tysabri, novantrone, donezepil HCL, rivastigmine, galantamine, memantine, levodopa, carbidopa, parlodel, permax, requip, mirapex, symmetrel, artane, cogentin, eldepryl, deprenyl, ZD6474, and INCB3619. Numerous other examples of active agents will be apparent to the skilled artisan.

An active agent can be administered to a patient from about 5 minutes to about 6 hours after administration of the peptide (e.g., about 5 minutes to about 5.5 hours; about 5 minutes to about 5 hours; about 5 minutes to about 4.5 hours; about 5 minutes to about 4 hours; about 5 minutes to about 3.5 hours; about 5 minutes to about 3 hours; about 5 minutes to about 2 hours; about 5 minutes to about 1.5 hours; about 5 minutes to about 1 hour; about 5 minutes to about 45 minutes; about 5 minutes to about 35 minutes; about 5 minutes to about 30 minutes; about 5 minutes to about 25 minutes; about 5 minutes to about 20 minutes; about 5 minutes to about 15 minutes; about 10 minutes to about 6 hours; about 15 minutes to about 6 hours; about 30 minutes to about 6 hours; about 45 minutes to about 6 hours; about 1 hour to about 6 hours; about 1.5 hours to about 6 hours; about 2 hours to about 6 hours; about 3 hours to about 6 hours; about 10 minutes to about 1 hour; about 15 minutes to about 45 minutes; about 20 minutes to about 50 minutes; about 30 minutes to about 1.5 hours; about 25 minutes to about 55 minutes; and about 10 minutes to about 30 minutes). For example, an active agent can be administered to a patient from about 5 minutes to about 2 hours after administration of the peptide. In some embodiments, an active agent is administered to a patient from about 10 minutes to about 1 hour after administration of the peptide.

A peptide as described herein and an immunoglobulin (and, optionally, an active agent) can be administered by any route, e.g., intravenous (IV), intramuscular, subcutaneous, oral, intranasal, inhalation, transdermal, and parenteral. In some embodiments, a peptide and immunoglobulin are administered by IV.

The specific dose of a peptide as described herein, an immunoglobulin, and/or an active agent will, of course, be determined by the particular circumstances of the individual patient including the size, weight, age and sex of the patient, the nature and stage of the disease being treated, the aggressiveness of the disease disorder, and the route of administration of the compound.

A "therapeutically effective" amount of an immunoglobulin (e.g., a therapeutic immunoglobulin), or of an additional active agent (e.g., a therapeutic agent) provided herein is typically one which is sufficient to achieve the desired effect and may vary according to the nature and severity of the disease condition, and the potency of the agent. It will be appreciated that different concentrations may be employed for prophylaxis than for treatment of an active disease.

An "effective amount" of an active agent (e.g., an imaging agent) provided herein is typically one which is sufficient to the desired effect of the agent (e.g., detection of an imaging agent) and may vary according to the detection method utilized and the detection limit of the agent.

Pharmaceutical Compositions

Provided herein are pharmaceutical compositions including a peptide as described herein. In some embodiments, a pharmaceutical composition including a peptide as described herein can also contain an immunoglobulin and/or an active agent. In some embodiments, a pharmaceutical composition can contain a complex including a peptide described herein and an immunoglobulin described herein, and a pharmaceutically acceptable carrier.

The pharmaceutical compositions provided herein contain a peptide as described herein, an immunoglobulin, and/or an active agent in an amount that results in transportation of the immunoglobulin across the BBB, and a pharmaceutically acceptable carrier. Pharmaceutical carriers suitable for administration of a peptide, an immunoglobulin, and/or an active agent provided herein include any such carriers known to those skilled in the art to be suitable for the particular mode of administration.

A pharmaceutically acceptable carrier can be selected on the basis of the selected route of administration and standard pharmaceutical practice. For example, the compositions can be formulated into suitable pharmaceutical preparations such as solutions, suspensions, tablets, dispersible tablets, pills, capsules, powders, sustained release formulations or elixirs, for oral administration or in sterile solutions or suspensions for parenteral administration and intraperitoneal injection, as well as transdermal patch preparation, dry powder inhalers, and ointments (see, e.g., Ansel, *Introduction to Pharmaceutical Dosage Forms*, Fourth Edition 1985, 126). A peptide and/or an immunoglobulin may be formulated into dosage forms according to standard practices in the field of pharmaceutical preparations. See Alphonso Gennaro, ed., *Remington's Pharmaceutical Sciences,* 18th Edition (1990), Mack Publishing Co., Easton, Pa.

For parenteral administration, a pharmaceutical composition can include a suitable carrier or diluent such as water, an oil (particularly a vegetable oil), ethanol, saline solution, aqueous dextrose (glucose) and related sugar solutions, glycerol, or a glycol such as propylene glycol or polyethylene glycol. Solutions for parenteral administration preferably contain a water soluble salt of a peptide and/or an active agent. Stabilizing agents, antioxidant agents and preservatives may also be added. Suitable antioxidant agents include sulfite, ascorbic acid, citric acid and its salts, and sodium EDTA. Suitable preservatives include benzalkonium chloride, methyl- or propyl-paraben, and chlorbutanol. The composition for parenteral administration may take the form of an aqueous or non-aqueous solution, dispersion, suspension or emulsion.

For oral administration, a pharmaceutical composition can include one or more solid inactive ingredients for the preparation of tablets, capsules, pills, powders, granules or other suitable oral dosage forms. For example, a pharmaceutical composition can include at least one excipient such as fillers, binders, humectants, disintegrating agents, solution retarders, absorption accelerators, wetting agents absorbents or lubricating agents.

The concentration of an immunoglobulin and/or an active agent administered to the patient will depend on absorption, inactivation and excretion rates of the compounds, the physicochemical characteristics of the compounds, the dosage schedule, and amount administered as well as other factors known to those of skill in the art.

The pharmaceutical composition may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular patient, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. A peptide, an immunoglobulin, and/or an active agent is (are), in one embodiment, formulated and administered in unit-dosage forms or multiple-dosage forms. Unit-dose forms as used herein refers to physically discrete units suitable for human and animal patients and packaged individually as is known in the art. Each unit-dose contains a predetermined quantity of the peptide or active agent sufficient to produce the desired effect, in association with the required pharmaceutical carrier, vehicle, or diluent. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Liquid pharmaceutically administrable compositions can, for example, be prepared by dissolving, dispersing, or otherwise mixing a pharmaceutical composition as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, solubilizing agents, pH buffering agents and the like, for example, acetate, sodium citrate, cyclodextrine derivatives, sorbitan monolaurate, triethanolamine sodium acetate, triethanolamine oleate, and other such agents.

Actual methods of preparing such dosage forms are known, or will be apparent, to those skilled in this art; for example, see *Remington's Pharmaceutical Sciences*, Mack Publishing Company, Easton, Pa., $15^{th}$ Edition, 1975.

Dosage forms or compositions containing a peptide, an immunoglobulin, and/or an active agent in the range of 0.005% to 100% with the balance made up with a non-toxic carrier may be prepared. Methods for preparation of these compositions are known to those skilled in the art. The contemplated compositions may contain 0.001%-100% a peptide or an active agent, in one embodiment 0.1-95%, in another embodiment 75-85%.

Kits

Also provided herein are kits. Typically, a kit includes a peptide as provided herein. A kit can also contain one or more immunoglobulins and/or one or more active agents as provided herein. In some embodiments, a kit includes a peptide and an immunoglobulin, and/or an active agent. In some embodiments, a kit includes a complex including a peptide as provided herein and a therapeutic immunoglobulin as provided herein. In certain embodiments, a kit can include one or more delivery systems, e.g., for an immunoglobulin, active agent, peptide, or any combination thereof, and directions for use of the kit (e.g., instructions for administering to a patient). In some embodiments, a kit can include a syringe having a peptide and a syringe having an immunoglobulin as provided herein. In some embodiments, the kit can also include a syringe having an additional active agent (e.g., a imaging agent or a therapeutic agent) and an instruction that indicates that the peptide and immunoglobulin are to be administered to a patient prior to administration of the additional active agent.

The invention will be further described in the following examples, which do not limit the scope of the invention described in the claims.

EXAMPLES

Example 1: Transportation of an Immunoglobulin Across the BBB

A bipartite peptide (Apo-I) was created which specifically binds to the Fc-chain of an IgG and interacts with the low-density lipoprotein receptor (LDLR) present on the surface of endothelial cells of the blood-brain barrier (BBB).

To explore whether Apo-I transports an antibody across the BBB, the peptide or a peptide-cetuximab complex were first injected by IV followed by injection of Evan's Blue (EB; a routinely used small molecule blue dye with a molecular weight of 960.81) by IV into the femoral vein of a mouse. Cardiac perfusion was performed and the brains of the mice were removed and evaluated approximately 2 hours following injection of the dye. As a control, injection of EB only was used. The particulars of each administration are as follows:

1) ~40 μL 2% EB only was injected.
2) 300 μg of Apo-I was injected first, then ~40 μL 2% EB was injected.
3) 600 μg of Apo-I was injected first, then ~40 μL 2% EB was injected.
4) 600 μg of Apo-I was mixed with 200 μg cetuximab prior to injection and then injected first, then ~40 μL 2% EB was injected.

As is shown in FIG. 1, EB cannot reach the brain when delivered alone (evidenced by the absence of blue coloring in brain number 1), or when delivered with 300 μg of Apo-I (evidenced by the absence of blue coloring in brain number 2). The absence of blue coloring at low concentrations (e.g., 300 μg) of Apo-I suggests that low concentrations do not form enough pores at the BBB through which EB can pass to the brain in amounts that can be visually assessed.

Apo-I binds to an antibody (IgG) molecule and sufficient amounts of Apo-I can deliver the antibody to the brain as well as create a transient opening of the BBB, through which small molecules can be transported. When Apo-I alone is introduced into the bloodstream by itself, it binds to the IgG molecules present in blood, transports the IgG to the brain and also creates transient pores at the BBB through which other molecules (such as EB) can be transported to the brain. As is shown in FIG. 1, delivery of 600 μg Apo-I, when injected into the femoral vein, complexed with IgG present in the blood and created transient pores at the BBB, through which EB passed through to the brain. This is evidenced by brain number 3 showing the blue coloring of the EB dye. Delivery of 600 μg Apo-I pre-mixed with cetuximab and injected as above also allows passage of EB to the brain. This is evidenced by brain number 4 showing the blue coloring of the EB dye.

These results suggest that the carrier peptide can deliver an antibody (e.g., present in the blood or provided in a pre-mixed Apo-I/antibody complex) as well as other molecules/drugs to the brain. To deliver a specific antibody (e.g., a therapeutic IgG) to the brain, the antibody can be pre-mixed with Apo-I, and the resulting peptide/antibody complex can administered and, optionally, followed by administration of another molecule/drug, rendering brain-uptake of both the antibody and, optionally, the molecule (EB).

Example 2: Specific Transport of Antibodies Across the BBB

Two radiolabeled antibodies, herceptin (HER) and cetuximab (CTX) and radiolabeled bovine serum albumin (BSA) were injected intravenously into mice with and without 600 μg of ApoI. Six mice were present in each of the various test groups. One hour after injection, mice were sacrificed. Brains were collected and radioactivity measured using microSPECT imaging.

Figure 2:
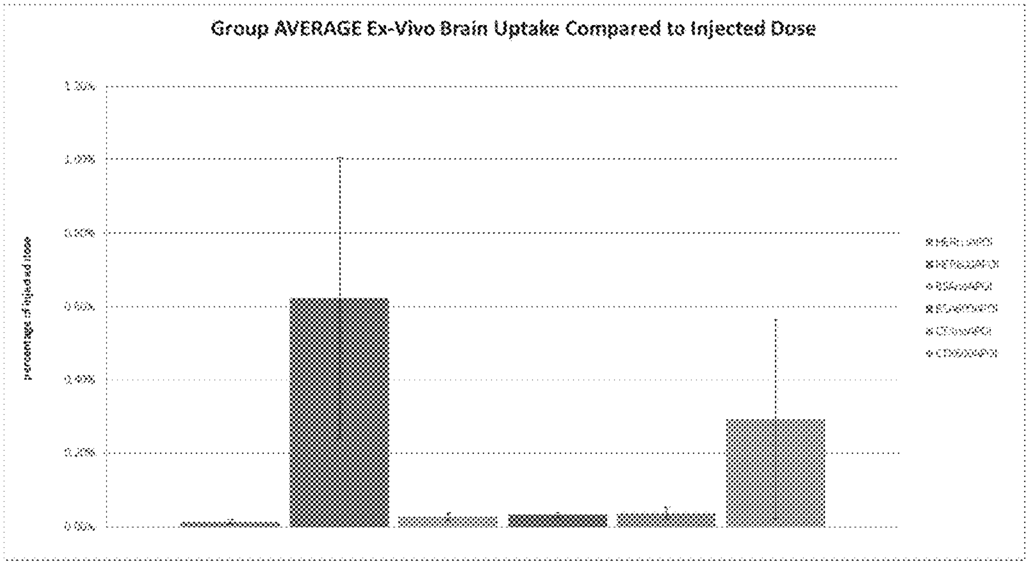
FIG. 2 is a bar graph illustrating the results of administration of two radiolabeled antibodies, herceptin (HER) and cetuximab (CTX), and one radiolabeled peptide, bovine serum albumin (BSA) with and without 600 μg ApoI into mice. The amount of the radiolabeled compound was detected using microSPECT imaging in collected brains. Samples in the figure legend occur in the graph from left to right.
Figure 3:
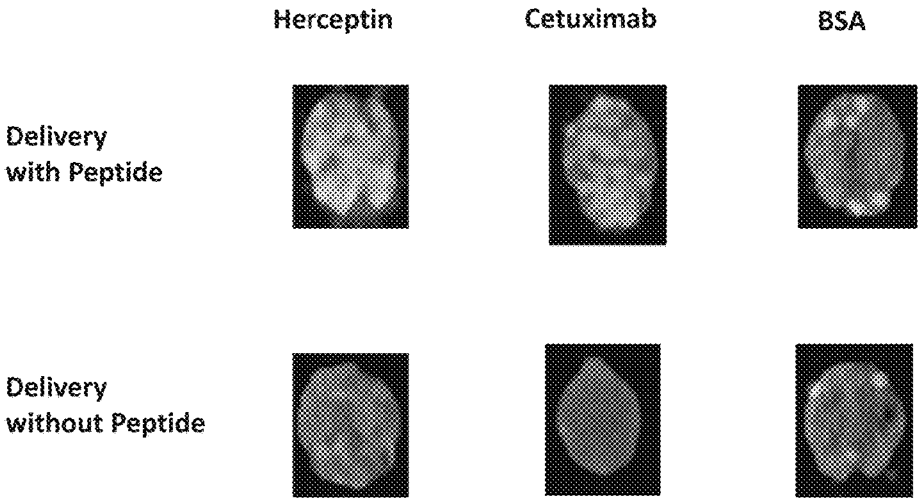
FIG. 3 shows microSPECT brain images following administration of two radiolabeled antibodies, herceptin (HER) and cetuximab (CTX), and one radiolabeled peptide, bovine serum albumin (BSA) with and without 600 μg ApoI into mice.

As seen in FIGS. 2 and 3, approximately 25-50-fold more antibody was delivered to the brain with the peptide than without. However, the ApoI polypeptide had no effect on brain-uptake of BSA, implying specificity of the peptide for the transportation of antibodies across the blood brain barrier.

OTHER EMBODIMENTS

It is to be understood that while the disclosure has been described in conjunction with the detailed description thereof, the foregoing description is intended to illustrate and not limit the scope of the disclosure, which is defined by the scope of the appended claims. Other aspects, advantages, and modifications are within the scope of the following claims.

---

What is claimed is:

1. A peptide comprising the sequence:

(SEQ ID NO: 1)

$A_p$-$L_n$-$B_m$ wherein:

(a) A is an immunoglobulin affinity ligand comprising the sequence H-W-R-G-W-Z (SEQ ID NO:26);

(b) L is a linker; and (c) B is a blood-brain barrier agent comprising the sequence:

(SEQ ID NO: 3)

L-R-X1-R-X2-X3-X4-H-L-R-X5-X6-X7-K-R-L-X8-R-D-X9;

wherein:

X1 is selected from the group consisting of A, L, S, and V;

X2 is selected from the group consisting of L and M;

X3 is selected from the group consisting of A and S;

X4 is selected from the group consisting of N, S, and T;

X5 is selected from the group consisting of K and N;

X6 is selected from the group consisting of L, M, and V;

X7 is selected from the group consisting of R and P;

X8 is selected from the group consisting of L and M;

X9 is selected from the group consisting of A and L;

n is an integer from 0 to 50;

m is an integer from 1 to 3; and p is an integer from 1 to 4.

2. The peptide of claim 1, wherein the immunoglobulin affinity ligand can non-covalently binds a therapeutic immunoglobulin.

3. The peptide of claim 2, wherein the therapeutic immunoglobulin is an IgG immunoglobulin.

4. The peptide of claim 1, wherein p is 1.

5. The peptide of claim 1, wherein the linker is one or more hydrophilic amino acids.

6. The peptide of claim 5, wherein the linker is one or more lysines.

7. The peptide of claim 6, wherein n is 4.

8. The peptide of claim 1, wherein the blood-brain barrier agent is (SEQ ID NO: 4)
L-R-V-R-L-A-S-H-L-R-K-L-R-K-R-L-L-R-D-A.

9. A complex comprising:

(a) the peptide of claim 1; and (b) a therapeutic immunoglobulin.

10. The complex of claim 9, wherein the blood-brain barrier agent is (SEQ ID NO: 4)
L-R-V-R-L-A-S-H-L-R-K-L-R-K-R-L-L-R-D-A.

11. The complex of claim 9, wherein the therapeutic immunoglobulin is selected from the group consisting of cetuximab, bococizumab, dinutuximab, racotumomab, ralpancizumab, and bevacizumab.

12. The complex of claim 9, where the peptide comprises the sequence:

(SEQ ID NO: 42)
H-W-R-G-W-Z-K-K-K-K-L-R-V-R-L-A-S-H-L-R-K-L-R-K-R-L-L-R-D-A.

13. A method of transporting a therapeutic immunoglobulin across the blood-brain barrier of a patient, the method comprising:

(a) administering to the patient an effective amount of a peptide comprising the sequence:

(SEQ ID NO: 1)
$A_p$-$L_n$-$B_m$ wherein:

i. A is an immunoglobulin affinity ligand comprising the sequence H-W-R-G-W-Z (SEQ ID NO:26);

ii. L is a linker; and iii. B is a blood-brain barrier agent comprising the sequence:

(SEQ ID NO: 3)
L-R-X1-R-X2-X3-X4-H-L-R-X5-X6-X7-K-R-L-X8-R-D-X9;

wherein:

X1 is selected from the group consisting of A, L, S, and V;

X2 is selected from the group consisting of L and M;

X3 is selected from the group consisting of A and S;

X4 is selected from the group consisting of N, S, and T;

X5 is selected from the group consisting of K and N;

X6 is selected from the group consisting of L, M, and V;

X7 is selected from the group consisting of R and P;

X8 is selected from the group consisting of L and M;

X9 is selected from the group consisting of A and L;

n is an integer from 0 to 50;

m is an integer from 1 to 3; and p is an integer from 1 to 4; and (b) concurrently administering to the patient an effective amount of the therapeutic immunoglobulin.

14. The method of claim 13, wherein the immunoglobulin affinity ligand non-covalently binds the therapeutic immunoglobulin.

15. The method of claim 14, wherein the therapeutic immunoglobulin is an IgG immunoglobulin.

16. A method of treating a neurological disorder in a patient, the method comprising:

(a) administering to the patient an effective amount of a peptide comprising the sequence:

(SEQ ID NO: 1)
$A_p$-$L_n$-$B_m$ wherein i. A is an immunoglobulin affinity ligand comprising the sequence H-W-R-G-W-Z (SEQ ID NO:26);

ii. L is a linker; and iii. B is a blood-brain barrier agent comprising the sequence:

(SEQ ID NO: 3)
L-R-X1-R-X2-X3-X4-H-L-R-X5-X6-X7-K-R-L-X8-R-D-X9;

wherein:

X1 is selected from the group consisting of A, L, S, and V;

X2 is selected from the group consisting of L and M;

X3 is selected from the group consisting of A and S;

X4 is selected from the group consisting of N, S, and T;

X5 is selected from the group consisting of K and N;

X6 is selected from the group consisting of L, M, and V;

X7 is selected from the group consisting of R and P;

X8 is selected from the group consisting of L and M;

X9 is selected from the group consisting of A and L;

n is an integer from 0 to 50;

m is an integer from 1 to 3; and p is an integer from 1 to 4; and (b) concurrently administering to the patient an effective amount of a therapeutic immunoglobulin.

17. The method of claim 16, wherein the neurological disorder is chosen from:

meningitis, epilepsy, multiple sclerosis, neuromyelitis optica, late-stage neurological trypanosomiasis, Parkinson's, progressive multifocal leukoencephalopathy, De Vivo disease, Alzheimer's disease, HIV Encephalitis, addiction, and cancer.

* * * * *

SEQUENCE LISTING

```
<160> NUMBER OF SEQ ID NOS: 43

<210> SEQ ID NO 1
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(24)
<223> OTHER INFORMATION: This region may encompass 1-4 'His Xaa Xaa Xaa
      Xaa Xaa' repeating units, wherein some positions may be absent
<220> FEATURE:
<221> NAME/KEY: MOD_RES
<222> LOCATION: (2)..(2)
<223> OTHER INFORMATION: Trp, Tyr or Phe
<220> FEATURE:
<221> NAME/KEY: MOD_RES
<222> LOCATION: (3)..(3)
<223> OTHER INFORMATION: Arg or Phe
<220> FEATURE:
<221> NAME/KEY: MOD_RES
<222> LOCATION: (4)..(4)
<223> OTHER INFORMATION: Gly, Lys or Arg
<220> FEATURE:
<221> NAME/KEY: MOD_RES
<222> LOCATION: (5)..(5)
<223> OTHER INFORMATION: Trp, Phe or His
<220> FEATURE:
<221> NAME/KEY: MOD_RES
<222> LOCATION: (6)..(6)
<223> OTHER INFORMATION: Glx, Val, Asp or Leu
<220> FEATURE:
<221> NAME/KEY: MOD_RES
<222> LOCATION: (8)..(8)
<223> OTHER INFORMATION: Trp, Tyr or Phe
<220> FEATURE:
<221> NAME/KEY: MOD_RES
<222> LOCATION: (9)..(9)
<223> OTHER INFORMATION: Arg or Phe
<220> FEATURE:
<221> NAME/KEY: MOD_RES
<222> LOCATION: (10)..(10)
<223> OTHER INFORMATION: Gly, Lys or Arg
<220> FEATURE:
<221> NAME/KEY: MOD_RES
<222> LOCATION: (11)..(11)
<223> OTHER INFORMATION: Trp, Phe or His
<220> FEATURE:
<221> NAME/KEY: MOD_RES
<222> LOCATION: (12)..(12)
<223> OTHER INFORMATION: Glx, Val, Asp or Leu
<220> FEATURE:
<221> NAME/KEY: MOD_RES
```

<222> LOCATION: (14)..(14)
<223> OTHER INFORMATION: Trp, Tyr or Phe
<220> FEATURE:
<221> NAME/KEY: MOD_RES
<222> LOCATION: (15)..(15)
<223> OTHER INFORMATION: Arg or Phe
<220> FEATURE:
<221> NAME/KEY: MOD_RES
<222> LOCATION: (16)..(16)
<223> OTHER INFORMATION: Gly, Lys or Arg
<220> FEATURE:
<221> NAME/KEY: MOD_RES
<222> LOCATION: (17)..(17)
<223> OTHER INFORMATION: Trp, Phe or His
<220> FEATURE:
<221> NAME/KEY: MOD_RES
<222> LOCATION: (18)..(18)
<223> OTHER INFORMATION: Glx, Val, Asp or Leu
<220> FEATURE:
<221> NAME/KEY: MOD_RES
<222> LOCATION: (20)..(20)
<223> OTHER INFORMATION: Trp, Tyr or Phe
<220> FEATURE:
<221> NAME/KEY: MOD_RES
<222> LOCATION: (21)..(21)
<223> OTHER INFORMATION: Arg or Phe
<220> FEATURE:
<221> NAME/KEY: MOD_RES
<222> LOCATION: (22)..(22)
<223> OTHER INFORMATION: Gly, Lys or Arg
<220> FEATURE:
<221> NAME/KEY: MOD_RES
<222> LOCATION: (23)..(23)
<223> OTHER INFORMATION: Trp, Phe or His
<220> FEATURE:
<221> NAME/KEY: MOD_RES
<222> LOCATION: (24)..(24)
<223> OTHER INFORMATION: Glx, Val, Asp or Leu
<220> FEATURE:
<221> NAME/KEY: MOD_RES
<222> LOCATION: (25)..(74)
<223> OTHER INFORMATION: Any hydrophilic or neutral amino acid or amino acid analog
<220> FEATURE:
<221> NAME/KEY: MISC_FEATURE
<222> LOCATION: (25)..(74)
<223> OTHER INFORMATION: This region may encompass 0 to 50 amino acids, wherein some positions may be absent
<220> FEATURE:
<221> NAME/KEY: MISC_FEATURE
<222> LOCATION: (75)..(134)
<223> OTHER INFORMATION: This region may encompass 1-3 'Leu Arg Xaa Arg Xaa Xaa Xaa His Leu Arg Xaa Xaa Xaa Lys Arg Leu Xaa Arg Asp Xaa' repeating units, wherein some positions may be absent
<220> FEATURE:
<221> NAME/KEY: MOD_RES
<222> LOCATION: (77)..(77)
<223> OTHER INFORMATION: Ala, Leu, Ser or Val
<220> FEATURE:
<221> NAME/KEY: MOD_RES
<222> LOCATION: (79)..(79)
<223> OTHER INFORMATION: Leu or Met
<220> FEATURE:
<221> NAME/KEY: MOD_RES
<222> LOCATION: (80)..(80)
<223> OTHER INFORMATION: Ala or Ser
<220> FEATURE:
<221> NAME/KEY: MOD_RES
<222> LOCATION: (81)..(81)
<223> OTHER INFORMATION: Asn, Ser or Thr
<220> FEATURE:
<221> NAME/KEY: MOD_RES
<222> LOCATION: (85)..(85)
<223> OTHER INFORMATION: Lys or Asn
<220> FEATURE:
<221> NAME/KEY: MOD_RES
<222> LOCATION: (86)..(86)
<223> OTHER INFORMATION: Leu, Met or Val
<220> FEATURE:

```
<221> NAME/KEY: MOD_RES
<222> LOCATION: (87)..(87)
<223> OTHER INFORMATION: Arg or Pro
<220> FEATURE:
<221> NAME/KEY: MOD_RES
<222> LOCATION: (91)..(91)
<223> OTHER INFORMATION: Leu or Met
<220> FEATURE:
<221> NAME/KEY: MOD_RES
<222> LOCATION: (94)..(94)
<223> OTHER INFORMATION: Ala or Leu
<220> FEATURE:
<221> NAME/KEY: MOD_RES
<222> LOCATION: (97)..(97)
<223> OTHER INFORMATION: Ala, Leu, Ser or Val
<220> FEATURE:
<221> NAME/KEY: MOD_RES
<222> LOCATION: (99)..(99)
<223> OTHER INFORMATION: Leu or Met
<220> FEATURE:
<221> NAME/KEY: MOD_RES
<222> LOCATION: (100)..(100)
<223> OTHER INFORMATION: Ala or Ser
<220> FEATURE:
<221> NAME/KEY: MOD_RES
<222> LOCATION: (101)..(101)
<223> OTHER INFORMATION: Asn, Ser or Thr
<220> FEATURE:
<221> NAME/KEY: MOD_RES
<222> LOCATION: (105)..(105)
<223> OTHER INFORMATION: Lys or Asn
<220> FEATURE:
<221> NAME/KEY: MOD_RES
<222> LOCATION: (106)..(106)
<223> OTHER INFORMATION: Leu, Met or Val
<220> FEATURE:
<221> NAME/KEY: MOD_RES
<222> LOCATION: (107)..(107)
<223> OTHER INFORMATION: Arg or Pro
<220> FEATURE:
<221> NAME/KEY: MOD_RES
<222> LOCATION: (111)..(111)
<223> OTHER INFORMATION: Leu or Met
<220> FEATURE:
<221> NAME/KEY: MOD_RES
<222> LOCATION: (114)..(114)
<223> OTHER INFORMATION: Ala or Leu
<220> FEATURE:
<221> NAME/KEY: MOD_RES
<222> LOCATION: (117)..(117)
<223> OTHER INFORMATION: Ala, Leu, Ser or Val
<220> FEATURE:
<221> NAME/KEY: MOD_RES
<222> LOCATION: (119)..(119)
<223> OTHER INFORMATION: Leu or Met
<220> FEATURE:
<221> NAME/KEY: MOD_RES
<222> LOCATION: (120)..(120)
<223> OTHER INFORMATION: Ala or Ser
<220> FEATURE:
<221> NAME/KEY: MOD_RES
<222> LOCATION: (121)..(121)
<223> OTHER INFORMATION: Asn, Ser or Thr
<220> FEATURE:
<221> NAME/KEY: MOD_RES
<222> LOCATION: (125)..(125)
<223> OTHER INFORMATION: Lys or Asn
<220> FEATURE:
<221> NAME/KEY: MOD_RES
<222> LOCATION: (126)..(126)
<223> OTHER INFORMATION: Leu, Met or Val
<220> FEATURE:
<221> NAME/KEY: MOD_RES
<222> LOCATION: (127)..(127)
<223> OTHER INFORMATION: Arg or Pro
<220> FEATURE:
<221> NAME/KEY: MOD_RES
<222> LOCATION: (131)..(131)
<223> OTHER INFORMATION: Leu or Met
```

<220> FEATURE:
<221> NAME/KEY: MOD_RES
<222> LOCATION: (134)..(134)
<223> OTHER INFORMATION: Ala or Leu

<400> SEQUENCE: 1

His Xaa Xaa Xaa Xaa Xaa His Xaa Xaa Xaa Xaa Xaa His Xaa Xaa Xaa
1 5 10 15

Xaa Xaa His Xaa Xaa Xaa Xaa Xaa Xaa Xaa Xaa Xaa Xaa Xaa Xaa Xaa
20 25 30

Xaa Xaa Xaa Xaa Xaa Xaa Xaa Xaa Xaa Xaa Xaa Xaa Xaa Xaa Xaa Xaa
35 40 45

Xaa Xaa Xaa Xaa Xaa Xaa Xaa Xaa Xaa Xaa Xaa Xaa Xaa Xaa Xaa Xaa
50 55 60

Xaa Xaa Xaa Xaa Xaa Xaa Xaa Xaa Xaa Xaa Leu Arg Xaa Arg Xaa Xaa
65 70 75 80

Xaa His Leu Arg Xaa Xaa Xaa Lys Arg Leu Xaa Arg Asp Xaa Leu Arg
85 90 95

Xaa Arg Xaa Xaa Xaa His Leu Arg Xaa Xaa Xaa Lys Arg Leu Xaa Arg
100 105 110

Asp Xaa Leu Arg Xaa Arg Xaa Xaa Xaa His Leu Arg Xaa Xaa Xaa Lys
115 120 125

Arg Leu Xaa Arg Asp Xaa
130

<210> SEQ ID NO 2
<211> LENGTH: 134
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MISC_FEATURE
<222> LOCATION: (1)..(60)
<223> OTHER INFORMATION: This region may encompass 1-3 'Leu Arg Xaa Arg Xaa Xaa Xaa His Leu Arg Xaa Xaa Xaa Lys Arg Leu Xaa Arg Asp Xaa' repeating units, wherein some positions may be absent
<220> FEATURE:
<221> NAME/KEY: MOD_RES
<222> LOCATION: (3)..(3)
<223> OTHER INFORMATION: Ala, Leu, Ser or Val
<220> FEATURE:
<221> NAME/KEY: MOD_RES
<222> LOCATION: (5)..(5)
<223> OTHER INFORMATION: Leu or Met
<220> FEATURE:
<221> NAME/KEY: MOD_RES
<222> LOCATION: (6)..(6)
<223> OTHER INFORMATION: Ala or Ser
<220> FEATURE:
<221> NAME/KEY: MOD_RES
<222> LOCATION: (7)..(7)
<223> OTHER INFORMATION: Asn, Ser or Thr
<220> FEATURE:
<221> NAME/KEY: MOD_RES
<222> LOCATION: (11)..(11)
<223> OTHER INFORMATION: Lys or Asn
<220> FEATURE:
<221> NAME/KEY: MOD_RES
<222> LOCATION: (12)..(12)
<223> OTHER INFORMATION: Leu, Met or Val
<220> FEATURE:
<221> NAME/KEY: MOD_RES
<222> LOCATION: (13)..(13)
<223> OTHER INFORMATION: Arg or Pro
<220> FEATURE:
<221> NAME/KEY: MOD_RES
<222> LOCATION: (17)..(17)

<223> OTHER INFORMATION: Leu or Met
<220> FEATURE:
<221> NAME/KEY: MOD_RES
<222> LOCATION: (20)..(20)
<223> OTHER INFORMATION: Ala or Leu
<220> FEATURE:
<221> NAME/KEY: MOD_RES
<222> LOCATION: (23)..(23)
<223> OTHER INFORMATION: Ala, Leu, Ser or Val
<220> FEATURE:
<221> NAME/KEY: MOD_RES
<222> LOCATION: (25)..(25)
<223> OTHER INFORMATION: Leu or Met
<220> FEATURE:
<221> NAME/KEY: MOD_RES
<222> LOCATION: (26)..(26)
<223> OTHER INFORMATION: Ala or Ser
<220> FEATURE:
<221> NAME/KEY: MOD_RES
<222> LOCATION: (27)..(27)
<223> OTHER INFORMATION: Asn, Ser or Thr
<220> FEATURE:
<221> NAME/KEY: MOD_RES
<222> LOCATION: (31)..(31)
<223> OTHER INFORMATION: Lys or Asn
<220> FEATURE:
<221> NAME/KEY: MOD_RES
<222> LOCATION: (32)..(32)
<223> OTHER INFORMATION: Leu, Met or Val
<220> FEATURE:
<221> NAME/KEY: MOD_RES
<222> LOCATION: (33)..(33)
<223> OTHER INFORMATION: Arg or Pro
<220> FEATURE:
<221> NAME/KEY: MOD_RES
<222> LOCATION: (37)..(37)
<223> OTHER INFORMATION: Leu or Met
<220> FEATURE:
<221> NAME/KEY: MOD_RES
<222> LOCATION: (40)..(40)
<223> OTHER INFORMATION: Ala or Leu
<220> FEATURE:
<221> NAME/KEY: MOD_RES
<222> LOCATION: (43)..(43)
<223> OTHER INFORMATION: Ala, Leu, Ser or Val
<220> FEATURE:
<221> NAME/KEY: MOD_RES
<222> LOCATION: (45)..(45)
<223> OTHER INFORMATION: Leu or Met
<220> FEATURE:
<221> NAME/KEY: MOD_RES
<222> LOCATION: (46)..(46)
<223> OTHER INFORMATION: Ala or Ser
<220> FEATURE:
<221> NAME/KEY: MOD_RES
<222> LOCATION: (47)..(47)
<223> OTHER INFORMATION: Asn, Ser or Thr
<220> FEATURE:
<221> NAME/KEY: MOD_RES
<222> LOCATION: (51)..(51)
<223> OTHER INFORMATION: Lys or Asn
<220> FEATURE:
<221> NAME/KEY: MOD_RES
<222> LOCATION: (52)..(52)
<223> OTHER INFORMATION: Leu, Met or Val
<220> FEATURE:
<221> NAME/KEY: MOD_RES
<222> LOCATION: (53)..(53)
<223> OTHER INFORMATION: Arg or Pro
<220> FEATURE:
<221> NAME/KEY: MOD_RES
<222> LOCATION: (57)..(57)
<223> OTHER INFORMATION: Leu or Met
<220> FEATURE:
<221> NAME/KEY: MOD_RES
<222> LOCATION: (60)..(60)
<223> OTHER INFORMATION: Ala or Leu
<220> FEATURE:
<221> NAME/KEY: MOD_RES

<222> LOCATION: (61)..(110)
<223> OTHER INFORMATION: Any hydrophilic or neutral amino acid or amino acid analog
<220> FEATURE:
<221> NAME/KEY: MISC_FEATURE
<222> LOCATION: (61)..(110)
<223> OTHER INFORMATION: This region may encompass 0 to 50 amino acids, wherein some positions may be absent
<220> FEATURE:
<221> NAME/KEY: MISC_FEATURE
<222> LOCATION: (111)..(134)
<223> OTHER INFORMATION: This region may encompass 1-4 'His Xaa Xaa Xaa Xaa Xaa' repeating units, wherein some positions may be absent
<220> FEATURE:
<221> NAME/KEY: MOD_RES
<222> LOCATION: (112)..(112)
<223> OTHER INFORMATION: Trp, Tyr or Phe
<220> FEATURE:
<221> NAME/KEY: MOD_RES
<222> LOCATION: (113)..(113)
<223> OTHER INFORMATION: Arg or Phe
<220> FEATURE:
<221> NAME/KEY: MOD_RES
<222> LOCATION: (114)..(114)
<223> OTHER INFORMATION: Gly, Lys or Arg
<220> FEATURE:
<221> NAME/KEY: MOD_RES
<222> LOCATION: (115)..(115)
<223> OTHER INFORMATION: Trp, Phe or His
<220> FEATURE:
<221> NAME/KEY: MOD_RES
<222> LOCATION: (116)..(116)
<223> OTHER INFORMATION: Glx, Val, Asp or Leu
<220> FEATURE:
<221> NAME/KEY: MOD_RES
<222> LOCATION: (118)..(118)
<223> OTHER INFORMATION: Trp, Tyr or Phe
<220> FEATURE:
<221> NAME/KEY: MOD_RES
<222> LOCATION: (119)..(119)
<223> OTHER INFORMATION: Arg or Phe
<220> FEATURE:
<221> NAME/KEY: MOD_RES
<222> LOCATION: (120)..(120)
<223> OTHER INFORMATION: Gly, Lys or Arg
<220> FEATURE:
<221> NAME/KEY: MOD_RES
<222> LOCATION: (121)..(121)
<223> OTHER INFORMATION: Trp, Phe or His
<220> FEATURE:
<221> NAME/KEY: MOD_RES
<222> LOCATION: (122)..(122)
<223> OTHER INFORMATION: Glx, Val, Asp or Leu
<220> FEATURE:
<221> NAME/KEY: MOD_RES
<222> LOCATION: (124)..(124)
<223> OTHER INFORMATION: Trp, Tyr or Phe
<220> FEATURE:
<221> NAME/KEY: MOD_RES
<222> LOCATION: (125)..(125)
<223> OTHER INFORMATION: Arg or Phe
<220> FEATURE:
<221> NAME/KEY: MOD_RES
<222> LOCATION: (126)..(126)
<223> OTHER INFORMATION: Gly, Lys or Arg
<220> FEATURE:
<221> NAME/KEY: MOD_RES
<222> LOCATION: (127)..(127)
<223> OTHER INFORMATION: Trp, Phe or His
<220> FEATURE:
<221> NAME/KEY: MOD_RES
<222> LOCATION: (128)..(128)
<223> OTHER INFORMATION: Glx, Val, Asp or Leu
<220> FEATURE:
<221> NAME/KEY: MOD_RES
<222> LOCATION: (130)..(130)
<223> OTHER INFORMATION: Trp, Tyr or Phe
<220> FEATURE:
<221> NAME/KEY: MOD_RES
<222> LOCATION: (131)..(131)
<223> OTHER INFORMATION: Arg or Phe
<220> FEATURE:
<221> NAME/KEY: MOD_RES
<222> LOCATION: (132)..(132)
<223> OTHER INFORMATION: Gly, Lys or Arg
<220> FEATURE:
<221> NAME/KEY: MOD_RES
<222> LOCATION: (133)..(133)
<223> OTHER INFORMATION: Trp, Phe or His
<220> FEATURE:
<221> NAME/KEY: MOD_RES
<222> LOCATION: (134)..(134)
<223> OTHER INFORMATION: Glx, Val, Asp or Leu

<400> SEQUENCE: 2

```
Leu Arg Xaa Arg Xaa Xaa Xaa His Leu Arg Xaa Xaa Xaa Lys Arg Leu
1               5                   10                  15

Xaa Arg Asp Xaa Leu Arg Xaa Arg Xaa Xaa Xaa His Leu Arg Xaa Xaa
            20                  25                  30

Xaa Lys Arg Leu Xaa Arg Asp Xaa Leu Arg Xaa Arg Xaa Xaa Xaa His
        35                  40                  45

Leu Arg Xaa Xaa Xaa Lys Arg Leu Xaa Arg Asp Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa His Xaa
            100                 105                 110

Xaa Xaa Xaa Xaa His Xaa Xaa Xaa Xaa Xaa His Xaa Xaa Xaa Xaa Xaa
        115                 120                 125

His Xaa Xaa Xaa Xaa Xaa
    130
```

<210> SEQ ID NO 3
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ala, Leu, Ser or Val
<220> FEATURE:
<221> NAME/KEY: MOD_RES
<222> LOCATION: (5)..(5)
<223> OTHER INFORMATION: Leu or Met
<220> FEATURE:
<221> NAME/KEY: MOD_RES
<222> LOCATION: (6)..(6)
<223> OTHER INFORMATION: Ala or Ser
<220> FEATURE:
<221> NAME/KEY: MOD_RES
<222> LOCATION: (7)..(7)
<223> OTHER INFORMATION: Asn, Ser or Thr
<220> FEATURE:
<221> NAME/KEY: MOD_RES
<222> LOCATION: (11)..(11)
<223> OTHER INFORMATION: Lys or Asn
<220> FEATURE:
<221> NAME/KEY: MOD_RES
<222> LOCATION: (12)..(12)
<223> OTHER INFORMATION: Leu, Met or Val
<220> FEATURE:
<221> NAME/KEY: MOD_RES
<222> LOCATION: (13)..(13)

```
<223> OTHER INFORMATION: Arg or Pro
<220> FEATURE:
<221> NAME/KEY: MOD_RES
<222> LOCATION: (17)..(17)
<223> OTHER INFORMATION: Leu or Met
<220> FEATURE:
<221> NAME/KEY: MOD_RES
<222> LOCATION: (20)..(20)
<223> OTHER INFORMATION: Ala or Leu

<400> SEQUENCE: 3

Leu Arg Xaa Arg Xaa Xaa Xaa His Leu Arg Xaa Xaa Xaa Lys Arg Leu
1               5                   10                  15

Xaa Arg Asp Xaa
            20


<210> SEQ ID NO 4
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Leu Arg Val Arg Leu Ala Ser His Leu Arg Lys Leu Arg Lys Arg Leu
1               5                   10                  15

Leu Arg Asp Ala
            20


<210> SEQ ID NO 5
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Leu Arg Ser Arg Leu Ala Ser His Leu Arg Lys Leu Arg Lys Arg Leu
1               5                   10                  15

Leu Arg Asp Ala
            20


<210> SEQ ID NO 6
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Leu Arg Val Arg Met Ala Ser His Leu Arg Lys Leu Arg Lys Arg Leu
1               5                   10                  15

Leu Arg Asp Ala
            20


<210> SEQ ID NO 7
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7
```

Leu Arg Val Arg Leu Ala Thr His Leu Arg Lys Leu Arg Lys Arg Leu
1 5 10 15

Leu Arg Asp Ala
20

<210> SEQ ID NO 8
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 8

Leu Arg Val Arg Leu Ala Ser His Leu Arg Lys Leu Pro Lys Arg Leu
1 5 10 15

Leu Arg Asp Ala
20

<210> SEQ ID NO 9
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 9

Leu Arg Val Arg Leu Ala Ser His Leu Arg Lys Leu Arg Lys Arg Leu
1 5 10 15

Met Arg Asp Ala
20

<210> SEQ ID NO 10
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 10

Leu Arg Val Arg Leu Ala Ser His Leu Arg Asn Leu Arg Lys Arg Leu
1 5 10 15

Leu Arg Asp Ala
20

<210> SEQ ID NO 11
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 11

Leu Arg Val Arg Leu Ala Ser His Leu Arg Lys Val Arg Lys Arg Leu
1 5 10 15

Leu Arg Asp Ala
20

<210> SEQ ID NO 12
<211> LENGTH: 20
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 12

Leu Arg Val Arg Met Ser Ser His Leu Arg Lys Leu Arg Lys Arg Leu
1 5 10 15

Leu Arg Asp Ala
20

<210> SEQ ID NO 13
<211> LENGTH: 20
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 13

Leu Arg Val Arg Leu Ala Ser His Leu Arg Asn Val Arg Lys Arg Leu
1 5 10 15

Leu Arg Asp Ala
20

<210> SEQ ID NO 14
<211> LENGTH: 20
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 14

Leu Arg Val Arg Leu Ala Ser His Leu Arg Asn Met Arg Lys Arg Leu
1 5 10 15

Leu Arg Asp Ala
20

<210> SEQ ID NO 15
<211> LENGTH: 20
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 15

Leu Arg Ala Arg Met Ala Ser His Leu Arg Lys Leu Arg Lys Arg Leu
1 5 10 15

Leu Arg Asp Ala
20

<210> SEQ ID NO 16
<211> LENGTH: 20
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 16

Leu Arg Val Arg Leu Ser Ser His Leu Arg Lys Leu Arg Lys Arg Leu
1 5 10 15

Met Arg Asp Ala

20

<210> SEQ ID NO 17
<211> LENGTH: 20
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 17

Leu Arg Ser Arg Leu Ala Ser His Leu Arg Lys Leu Arg Lys Arg Leu
1 5 10 15

Met Arg Asp Ala
20

<210> SEQ ID NO 18
<211> LENGTH: 20
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 18

Leu Arg Val Arg Leu Ser Ser His Leu Pro Lys Leu Arg Lys Arg Leu
1 5 10 15

Leu Arg Asp Ala
20

<210> SEQ ID NO 19
<211> LENGTH: 20
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 19

Leu Arg Val Arg Leu Ser Ser His Leu Arg Lys Leu Pro Lys Arg Leu
1 5 10 15

Leu Arg Asp Ala
20

<210> SEQ ID NO 20
<211> LENGTH: 20
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 20

Leu Arg Val Arg Leu Ala Ser His Leu Arg Lys Met Arg Lys Arg Leu
1 5 10 15

Met Arg Asp Ala
20

<210> SEQ ID NO 21
<211> LENGTH: 20
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 21

Leu Arg Val Arg Leu Ala Ser His Leu Arg Asn Leu Pro Lys Arg Leu
1 5 10 15

Leu Arg Asp Ala
20

<210> SEQ ID NO 22
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 22

Leu Arg Leu Arg Leu Ala Asn His Leu Arg Lys Leu Arg Lys Arg Leu
1 5 10 15

Leu Arg Asp Ala
20

<210> SEQ ID NO 23
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 23

Leu Arg Leu Arg Leu Ala Ser His Leu Arg Lys Leu Arg Lys Arg Leu
1 5 10 15

Leu Arg Asp Leu
20

<210> SEQ ID NO 24
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 24

Leu Arg Val Arg Leu Ala Asn His Leu Arg Lys Leu Arg Lys Arg Leu
1 5 10 15

Leu Arg Asp Leu
20

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (2)..(2)
<223> OTHER INFORMATION: Trp, Tyr or Phe
<220> FEATURE:
<221> NAME/KEY: MOD_RES
<222> LOCATION: (3)..(3)
<223> OTHER INFORMATION: Arg or Phe
<220> FEATURE:
<221> NAME/KEY: MOD_RES
<222> LOCATION: (4)..(4)
<223> OTHER INFORMATION: Gly, Lys or Arg
<220> FEATURE:
<221> NAME/KEY: MOD_RES
<222> LOCATION: (5)..(5)
<223> OTHER INFORMATION: Trp, Phe or His
<220> FEATURE:
<221> NAME/KEY: MOD_RES
<222> LOCATION: (6)..(6)
<223> OTHER INFORMATION: Glx, Val, Asp or Leu

<400> SEQUENCE: 25

His Xaa Xaa Xaa Xaa Xaa
1               5

<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

His Trp Arg Gly Trp Glx
1               5

<210> SEQ ID NO 27
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

His Trp Arg Gly Trp Val
1               5

<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

His Trp Arg Gly Trp Val
1               5

<210> SEQ ID NO 29
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

His Tyr Phe Lys Phe Asp
1               5

<210> SEQ ID NO 30
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

His Phe Arg Arg His Leu
1 5

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 31

Gln Asn Ala Phe Tyr Glu Ile Leu
1 5

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 32

Tyr Asp Trp Ile Pro Ser Ser Ala Trp
1 5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 33

Ala Gly Ala Ile Trp Gln Arg Asp Trp
1 5

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 34

Ser Trp Ile Ser Ser Arg Asp Trp Thr
1 5

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 35

Glu Ala Asx Tyr Ser Lys Asp Trp Leu
1 5

<210> SEQ ID NO 36
<211> LENGTH: 11
<212> TYPE: PRT

-continued

<213> ORGANISM: Artificial Sequence
<220> FEATURE:
<223> OTHER INFORMATION: Description of Artificial Sequence: Synthetic
      peptide

<400> SEQUENCE: 36

Asn Asp Asn Gly Val Asp Gly Glu Trp Thr Tyr
1               5                   10

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Asp Trp Ile Pro Gln Ala Ser Trp Glu
1               5

<210> SEQ ID NO 38
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Glu Pro Ile His Arg Ser Thr Leu Thr Ala Leu Leu
1               5                   10

<210> SEQ ID NO 39
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gly Phe Arg Lys Tyr Leu His Phe Arg Arg His Leu Leu
1               5                   10

<210> SEQ ID NO 40
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Val Arg Leu Gly Trp Leu Leu Ala Pro Ala Asp Leu Asp Ala Arg
1               5                   10                  15

<210> SEQ ID NO 41
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Trp, Tyr or Phe
<220> FEATURE:

<221> NAME/KEY: MOD_RES
<222> LOCATION: (3)..(3)
<223> OTHER INFORMATION: Arg or Phe
<220> FEATURE:
<221> NAME/KEY: MOD_RES
<222> LOCATION: (4)..(4)
<223> OTHER INFORMATION: Gly, Lys or Arg
<220> FEATURE:
<221> NAME/KEY: MOD_RES
<222> LOCATION: (5)..(5)
<223> OTHER INFORMATION: Trp, Phe or His
<220> FEATURE:
<221> NAME/KEY: MOD_RES
<222> LOCATION: (6)..(6)
<223> OTHER INFORMATION: Glx, Val, Asp or Leu
<220> FEATURE:
<221> NAME/KEY: MOD_RES
<222> LOCATION: (13)..(13)
<223> OTHER INFORMATION: Ala, Leu, Ser or Val
<220> FEATURE:
<221> NAME/KEY: MOD_RES
<222> LOCATION: (15)..(15)
<223> OTHER INFORMATION: Leu or Met
<220> FEATURE:
<221> NAME/KEY: MOD_RES
<222> LOCATION: (16)..(16)
<223> OTHER INFORMATION: Ala or Ser
<220> FEATURE:
<221> NAME/KEY: MOD_RES
<222> LOCATION: (17)..(17)
<223> OTHER INFORMATION: Asn, Ser or Thr
<220> FEATURE:
<221> NAME/KEY: MOD_RES
<222> LOCATION: (21)..(21)
<223> OTHER INFORMATION: Lys or Asn
<220> FEATURE:
<221> NAME/KEY: MOD_RES
<222> LOCATION: (22)..(22)
<223> OTHER INFORMATION: Leu, Met or Val
<220> FEATURE:
<221> NAME/KEY: MOD_RES
<222> LOCATION: (23)..(23)
<223> OTHER INFORMATION: Arg or Pro
<220> FEATURE:
<221> NAME/KEY: MOD_RES
<222> LOCATION: (27)..(27)
<223> OTHER INFORMATION: Leu or Met
<220> FEATURE:
<221> NAME/KEY: MOD_RES
<222> LOCATION: (30)..(30)
<223> OTHER INFORMATION: Ala or Leu

<400> SEQUENCE: 41

```
His Xaa Xaa Xaa Xaa Xaa Lys Lys Lys Lys Leu Arg Xaa Arg Xaa Xaa
1               5                   10                  15

Xaa His Leu Arg Xaa Xaa Xaa Lys Arg Leu Xaa Arg Asp Xaa
            20                  25                  30
```

<210> SEQ ID NO 42
<211> LENGTH: 28
<212> TYPE: PRT
<213> ORGANISM: Artificial Sequence
<220> FEATURE:
<223> OTHER INFORMATION: Description of Artificial Sequence: Synthetic peptide

<400> SEQUENCE: 42

```
Arg Gly Trp Glx Lys Lys Lys Lys Leu Arg Val Arg Leu Ala Ser His
1               5                   10                  15

Leu Arg Lys Leu Arg Lys Arg Leu Leu Arg Asp Ala
            20                  25
```

<210> SEQ ID NO 43

```
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (13)..(13)
<223> OTHER INFORMATION: Ala, Leu, Ser or Val
<220> FEATURE:
<221> NAME/KEY: MOD_RES
<222> LOCATION: (15)..(15)
<223> OTHER INFORMATION: Leu or Met
<220> FEATURE:
<221> NAME/KEY: MOD_RES
<222> LOCATION: (16)..(16)
<223> OTHER INFORMATION: Ala or Ser
<220> FEATURE:
<221> NAME/KEY: MOD_RES
<222> LOCATION: (17)..(17)
<223> OTHER INFORMATION: Asn, Ser or Thr
<220> FEATURE:
<221> NAME/KEY: MOD_RES
<222> LOCATION: (21)..(21)
<223> OTHER INFORMATION: Lys or Asn
<220> FEATURE:
<221> NAME/KEY: MOD_RES
<222> LOCATION: (22)..(22)
<223> OTHER INFORMATION: Leu, Met or Val
<220> FEATURE:
<221> NAME/KEY: MOD_RES
<222> LOCATION: (23)..(23)
<223> OTHER INFORMATION: Arg or Pro
<220> FEATURE:
<221> NAME/KEY: MOD_RES
<222> LOCATION: (27)..(27)
<223> OTHER INFORMATION: Leu or Met
<220> FEATURE:
<221> NAME/KEY: MOD_RES
<222> LOCATION: (30)..(30)
<223> OTHER INFORMATION: Ala or Leu

<400> SEQUENCE: 43

His Trp Arg Gly Trp Glx Lys Lys Lys Lys Leu Arg Xaa Arg Xaa Xaa
1               5                   10                  15

Xaa His Leu Arg Xaa Xaa Xaa Lys Arg Leu Xaa Arg Asp Xaa
            20                  25                  30
```